(12) United States Patent
Sage, Jr. et al.

(10) Patent No.: US 6,350,259 B1
(45) Date of Patent: Feb. 26, 2002

(54) SELECTED DRUG DELIVERY PROFILES USING COMPETING IONS

(75) Inventors: Burton H. Sage, Jr., Hot Springs Village, AR (US); Carl Randolph Bock, Durham, NC (US)

(73) Assignee: Vyteris, Inc., Fair Lawn, NJ (US)

( * ) Notice: Subject to any disclaimer, the term of this patent is extended or adjusted under 35 U.S.C. 154(b) by 0 days.

(21) Appl. No.: 09/480,540

(22) Filed: Jan. 10, 2000

Related U.S. Application Data

(63) Continuation-in-part of application No. 08/878,368, filed on Jun. 18, 1997, now abandoned.
(60) Provisional application No. 60/026,862, filed on Sep. 30, 1996.

(51) Int. Cl.[7] .............................................. A61M 31/00
(52) U.S. Cl. ..................................................... 604/501
(58) Field of Search .............................. 604/501, 20–21

(56) References Cited

U.S. PATENT DOCUMENTS

| | | | |
|---|---|---|---|
| 4,474,570 A | * | 10/1984 | Arivra et al. |
| 4,820,263 A | | 4/1989 | Spevak et al. |
| 4,927,408 A | | 5/1990 | Haak et al. |
| 5,084,008 A | | 1/1992 | Phipps |
| 5,169,382 A | | 12/1992 | Theeuwes et al. |
| 5,622,530 A | | 4/1997 | Phipps |

FOREIGN PATENT DOCUMENTS

EP      0 931 564 A1     7/1999

* cited by examiner

*Primary Examiner*—Mark Bockelman
(74) *Attorney, Agent, or Firm*—Kirkpatrick & Lockhart LLP

(57) ABSTRACT

The present invention relates to a non-invasive method and apparatus for pre selecting the drug delivery profile of a drug by controlling the concentration of ions added to or present in the reservoir containing the drug to be delivered, which ions would compete with the drug ions for the current.

36 Claims, 17 Drawing Sheets

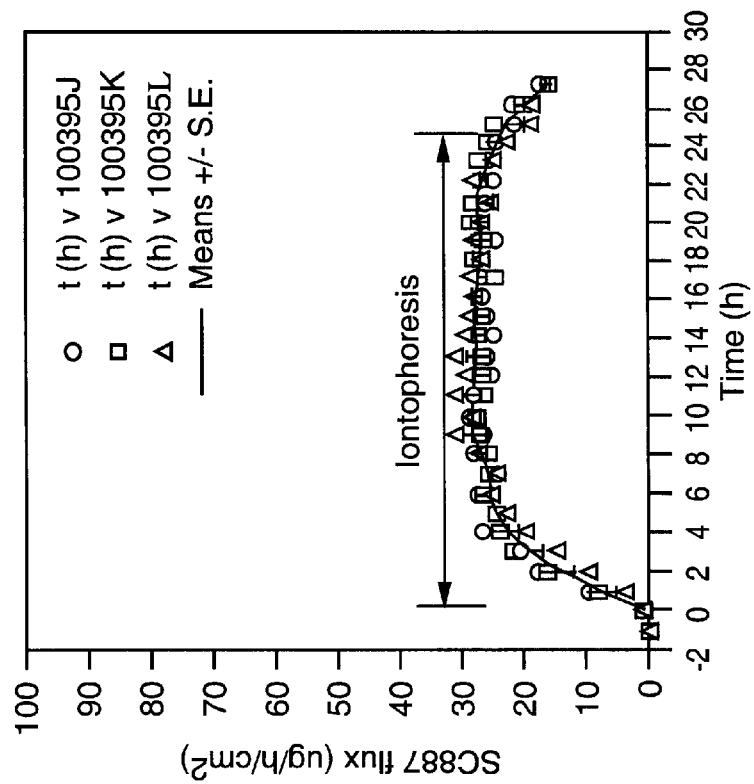
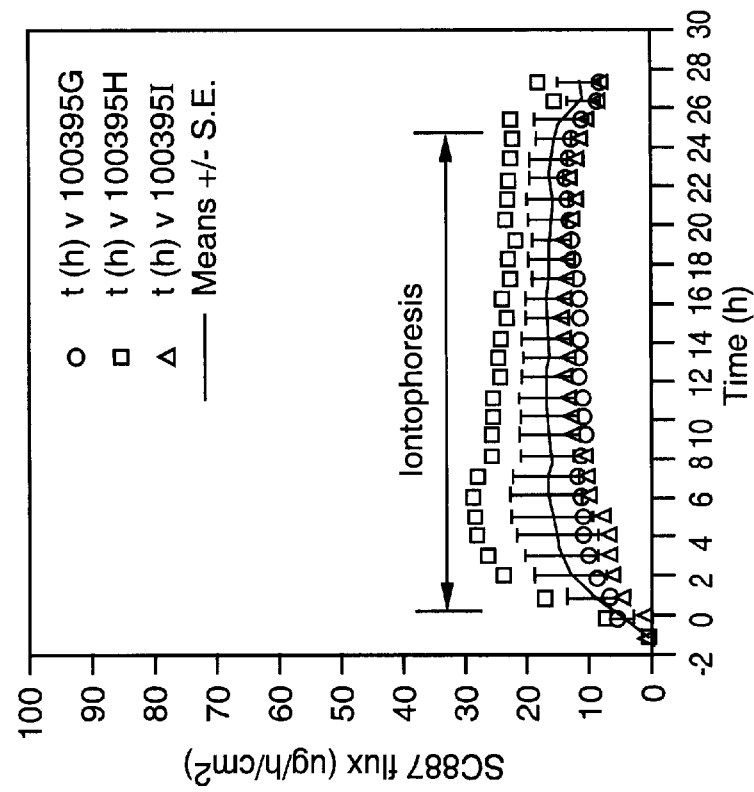
FIG. 10B
FIG. 10A

US 6,350,259 B1

SELECTED DRUG DELIVERY PROFILES USING COMPETING IONS

This application is a CIP of a U.S. application Ser. No. 08/878,368 filed Jun. 18, 1997, now abandoned, which is claims benefit to provisional application, Ser. No. 60/026,862 filed Sept. 30, 1996

FIELD OF INVENTION

The present invention relates to a non-invasive method and apparatus for pre selecting the drug delivery profile of a drug by controlling the concentration of ions added to or present in the reservoir containing the drug to be delivered, which ions would compete with the drug ions for the current.

BACKGROUND OF THE INVENTION

Iontophoretic drug delivery systems, have, in recent years, become an increasingly important means of administering drugs.

Presently there are two types of transdermal drug delivery systems, i.e., passive and iontophoretic. Passive patch systems deliver small and relatively lipophilic drugs through the skin of the patient by diffusion, an example of which would involve the application of the Duragesic® patch which releases the narcotic analgesic, fentanyl, to provide pain relief Iontophoresis systems, on the other hand, deliver drug through the skin of the patient through the application of an electromotive force (iontophoresis) to drive ionizable substances (medicament/drug) into the skin so that they can be absorbed by adjacent tissues and blood vessels. Iontophoresis, therefore, allows charged and hydrophilic drugs to be transported across the skin which are poorly deliverable through passive diffusion. Transdermal systems offer advantages clearly not achievable by other modes of administration, such as hypodermic injection which has the associated problem of pain, risk of infection and trauma to the patient Iontophoresis also has advantages over oral administration in that continuous and prolonged delivery can be achieved. In addition inactivation of the medicament, food interactions, first pass hepatic metabolism and gastrointestinal side effects may be avoided.

Conventional iontophoretic devices, such as those described in U.S. Pat. Nos. 4,820,263 (Spevak, et al.), 4,927,408 (Haak, et al.) and 5,084,008 (Phipps), the disclosures of which are hereby incorporated by reference, provide for delivery of a drug or medicament transdernally through iontophoresis. Basically, conventional iontophoretic devices consist of a power source connected to two electrodes, an anode and a cathode, which are individually in ionic contact with an electrolyte or drug reservoir which is in contact with the skin to be treated by the iontophoretic device. When the current is turned on, electrical energy is used to assist in the transport of ionic molecules into the body through the skin, via ionic conduction.

In general, the flux of a drug across the skin from an iontophoretic device is proportional to current, thus, a way to obtain varied flux or drug delivery profiles would be to vary the current. By way of example, if one wanted to administer a bolus-like (or peaked) flux, one would need to increase the current at first and then decrease the current after the bolus has been achieved. However, to vary the current adds complexities to the iontophoresis control circuit and it also increases the likelihood that the patient will feel sensation due to the changes in the current being administered.

The method and apparatus of the present invention overcomes these shortcomings and provides a method and apparatus for pre-selecting or controlling the drug delivery of flux profile of a drug being iontophoretically delivered.

SUMMARY OF THE INVENTION

One embodiment of the present invention provides a method for controlling the flux profile of drug delivered by iontophoresis by, prior to ionthophoretic delivery adding to or having present in the reservoir containing the drug, ions which would compete with the drug ions for current (hereinafter referred to as "competing ions"). To achieve various flux profiles for the drug being delivered, one may use constant current, thus avoiding the shortcomings of prior methods, but vary the concentration of the competing ions.

Another embodiment of the present invention provides for an iontophoretic device for controlling the flux profile of drug delivered by iontophoresis by, prior to iontophoretic delivery, adding to or having present in the reservoir containing the drug, ions which would compete with the drug ions for current. The iontophoretic device has (a) a current distributing member;

(b) an ionized substance reservoir containing an ionized or ionizable substance, in electrical communication with the current distributing member and adapted to be placed in ionic communication with the epithelial surface of a subject;

(c) an electrolyte reservoir containing an electrolyte, in electrical communication with an indifference electrode and in ionic communication with an epithelial surface; and (d) an electrical power source in current delivering connection with the current distribution member and the electrolyte reservoir.

BRIEF DESCRIPTION OF THE FIGURES

FIG. 10A depicts the delivery rate profile of a dual compartment patch loaded with a 250 mM NaCl, 50 mg/mL formulation and run at a current of 250 µA.

FIG. 10B depicts the delivery rate profile of a dual compartment patch loaded with a 250 mM NaCl, 150 mg/mL formulation and run at a current of 250 µA.

DETAILED DESCRIPTION OF THE INVENTION

Figure 1:
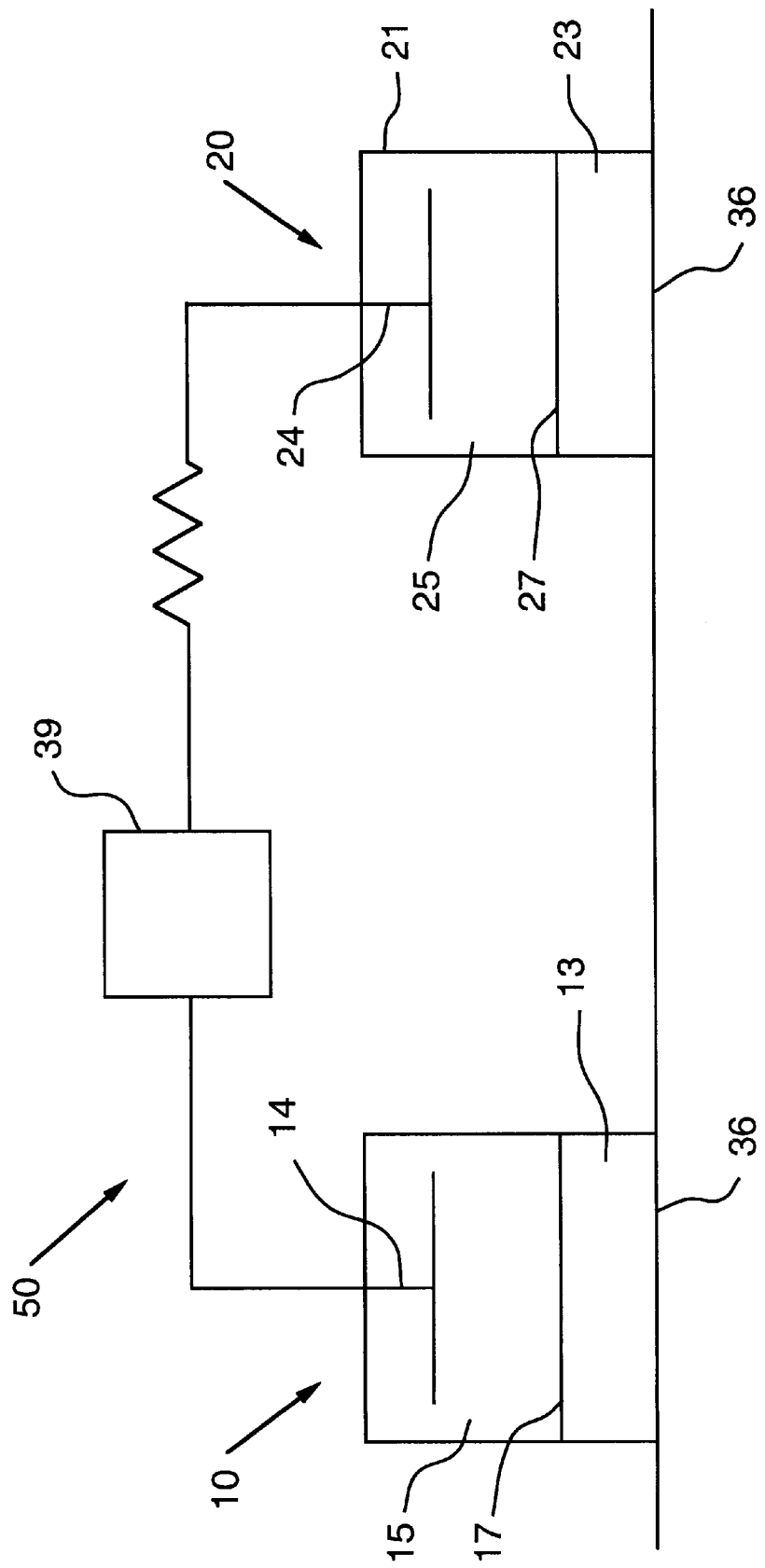
FIG. 1 depicts an embodiment of the iontophoretic device of the present invention.

One embodiment of the present invention provides a method for controlling the flux profile of drug delivered by iontophoresis by prior to iontophoretic delivery, adding to or having present in the reservoir containing the drug, ions which would compete with the drug ions for current. To achieve various flux profiles for the drug being delivered, one may use constant current but vary the concentration of the competing ions.

Another more specific embodiment provides for a method for controlling the flux profile of an iontophoretically delivered positively-charged ionic drug. A reservoir is formed containing the drug with a negatively-charged counter-ion and adding to the reservoir a concentration of cations which compete with the drug ions for carrying charge from the reservoir to the body surface of a patient. The concentration of cations is an amount sufficient for controlling the flux profile of the ionic drug. Preferably, the concentration of cations is an amount greater than about 0.06% and less than 1.0% by weight of electrolyte in the reservoir. More preferably, the concentration of cations is present in a range from about 0.146% (Example 9) to about 0.9% (Examples 6 and 12–14) by weight of electrolyte in the reservoir. An electrically conductive member is applied to the reservoir. The electrically conductive member is made up of a sacrificial material readily oxidizable when the conductive member is in contact with the reservoir and a positive voltage is applied to the conductive member. The material when oxidized readily combines with the counter-ion to form a compound which is substantially immobile within the reservoir during the application of the positive voltage.

The reservoir containing the ionic drug is placed in drug transmitting relation to the body surface of the patient. While the reservoir is in drug transmitting relation to the body surface of the patient and the conductive member is applied to the reservoir, a positive voltage is applied to the conductive member to oxidize the material and to drive the ionic drug through the body surface of the patient. At this time the ionic drug is driven through the body surface in the presence of cations which can compete with the drug ions for carrying charge from the reservoir.

Another more specific embodiment provides for a method for controlling the flux profile of an iontophoretically delivered negatively-charged ionic drug. A reservoir containing the drug with a positively-charged counter-ion is formed and a concentration of anions which compete with the drug ions for carrying charge from the reservoir to a body surface of a patient is added to the reservoir. The concentration of anions is an amount sufficient for controlling the flux profile of the ionic drug. Preferably, the concentration of anions is an amount greater than 0.06% and less than 1.0% by weight of electrolyte in the reservoir. More preferably, the concentration of anions is present in a range from about 0.146% (Example 9) to about 0.9% (Examples 6 and 12–14) by weight of electrolyte in the reservoir. An electrically conductive member is applied to the reservoir. The conductive member is made up of a sacrificial material readily reducible when the conductive member is in contact with the reservoir and a negative voltage is applied to the conductive member. The material when reduced is readily combined with the counter-ion to form a compound which is substantially immobile within the reservoir during the application of the negative voltage.

The reservoir containing the ionic drug is placed in drug transmitting relation to the body surface of the patient. While the reservoir is in drug transmitting relation to the body surface of the patient and the conductive member is applied to the reservoir, a negative voltage is applied to the conductive member to reduce the material and to drive the ionic drug through the body surface of the patient. The ionic drug is driven through the body surface in the presence of anions which can compete with the drug ions for carrying charge from the reservoir.

Another embodiment of the present invention provides for an iontophoretic device for controlling the flux profile of drug delivered by iontophoresis by, prior to iontophoretic delivery, adding to or having present in the reservoir containing the drug, ions which would compete with the drug ions for current. The iontophoretic device has (a) a current distributing member;

(b) an ionized substance reservoir containing an ionized or ionizable substance, in electrical communication with the current distributing member and adapted to be placed in ionic communication with the epithelial surface of a subject;

(c) an electrolyte reservoir containing an electrolyte, in electrical communication with an indifferent electrode and in ionic communication with the epithelial surface; and (d) an electrical power source in current delivering connection with the current distribution member and the electrolyte reservoir.

The iontophoretic device of the present invention may by way of example and not limitation include the following component and materials.

A. The Current Distributing Member (active electrode)

The iontophoretic electrode of the invention includes a current distributing member which conveys electrical current into the iontophoretic reservoirs for the delivery of an ionized substance. The current distributing member is constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes current without being eroded or depleted due to the distribution of current, and conducts current through generating ions by either reduction or oxidation of water. Inert conductive materials typically include, for example, stainless steel, platinum, gold, and carbon or graphite.

Alternatively, the current distributing member may be constructed from a sacrificial conductive material. A material may be considered sacrificial if, when employed as an electrode in an iontophoretic device of the invention, the material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal halide salt is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate electrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context.

Additional types of materials useful as current distributing members according to the invention are disclosed in detail in a co-pending application entitled Low-Cost Electrodes for an Iontophoretic Device, by V. Reddy et al., Serial No. 08/536,029, filed on Sept. 29, 1995, the disclosure of which is incorporated by reference herein.

The current distributing member may take any form known in the art, such as the form of a plate, foil layer, screen, wire, or dispersion of conductive particles embedded in a conductive matrix.

B. The Electrolyte Reservoir

1. Electrolytes

In the iontophoretic devices of the invention, an electrolyte reservoir is arranged in electrical communication with a current distributing member. Typically, electrical communication requires that electrons from the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface is preferably low.

The electrolyte reservoir comprises at least one electrolyte, i.e., an ionic or ionizable component which can act to conduct current toward or away from the current distributing member. Typically, the electrolyte comprises one or more mobile ions, the selection of which is dependent upon the desired application. Examples of suitable electrolytes include aqueous solutions of salts. A preferred electrolyte is an aqueous solution of NaCl, having concentration of less than 1 mole/liter (<1M), more preferably at about physiological concentration. Other electrolytes include salts of physiological ions including, but not limited to, potassium, ($K^+$), chloride ($Cl^{31}$), and phosphate ($PO_4^-$). The salt and its concentration may be selected as desired for particular applications. Other species may be selected by the skilled artisan for inclusion in the electrolyte reservoir. Such other reservoir species include, without limitation, chelation agents (e.g., citrate ions, EDTA) surfactants (e.g., non-ionic, zwitterionic, cationic, or anionic), buffers, ionic excipients, osmolarity adjusters (e.g., alkanols), stabilizers, enzyme inhibitors, preservatives, thickening agents (e.g., acrylic acids, cellulosic resins, clays, polyoxyethylenes), and the like.

Alternatively, the electrolyte may comprise a material which is itself relatively immobile in the absence of an electric field, but which acts to deliver mobile ions in the presence of an electric field. In the latter case, the electrolyte may more properly be termed an "ion source." Examples of ion sources according to the invention include polyelectrolytes, ion exchange membranes and resins, non-ionic buffers which become ionic upon pH change, and other known ion sources.

Alternatively, the electrolyte reservoir may contain counterions that form a soluble salt with an electrochemically generated ion. For example, in an apparatus employing a silver anodal current distributing member, a suitable counterion might be acetate or nitrate. Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

C. The Ionized Substance (Drug) Reservoir

The reservoir structure of the iontophoretic apparatus of the invention further includes an ionized substance reservoir. The ionized substance reservoir must be in ionic communication with an epithelial surface.

The construction of the ionized substance reservoir must be consistent with the requirements for ionic communication with the epithelial surface and electrical communication with the current distribution member. Accordingly, the structure of the ionized substance reservoir would vary, depending upon the desired application. The ionized substance reservoir may include a liquid, semi-liquid, semi-solid, or solid material. With a flowable material, the ionized substance reservoir preferably further comprises means for at least substantially inhibiting the flow of the contents out of the reservoir. In such situations, the flow of the contents is desirably minimized when the device is in storage. For example, a membrane may be deployed to surround the contents of the ionized substance reservoir. In certain situations the flow of the contents of the reservoir may be minimized while in storage, but increased in use. For example, a surrounding membrane may increase in porosity, permeability, or conductivity upon the application of an electric field across the membrane. Examples of such membranes are disclosed in U.S. Pat. Nos. 5,080,546; 5,169,382; and 5,232,428, the disclosures of which are incorporated by reference herein.

In preferred embodiments, the ionized substance reservoir is constructed to retain its physical integrity and to inherently resist migration and loss of the ionized substance. Such embodiments include those in which the ionized substance reservoir includes a solid or semi-solid material such as a gel or other polymeric material. In an especially preferred embodiment, the ionized substance reservoir includes a polymeric film in which the substance to be iontophoretically delivered is dispersed. The mobility of the substance to be delivered is substantially increased by the application of the electric field, permitting effective delivery across the target epithelial surface. Such a film need not contain any significant amount of hydrating material. In preferred embodiments, a cross-linked hydrogel in the electrolyte reservoir, because it inherently contains significant amounts of water, can serve as a water reservoir during iontophoresis.

It may be desirable to provide the solution of active ingredient with a buffer. The ion of the buffer of like charge to the drug ion should have low ionic mobility. The limiting ionic mobility of this ion is preferably no greater than $1 \times 10^{-4}$ cm$^2$/volt-sec. The ionized substance reservoir also contains an amount of an ion which will compete with the ionized or ionizable drug, the amount of the ion should be sufficient for controlling the flux profile of the ionized or ionizable drug being delivered. Preferably, the concentration of ions is an amount greater than about 0.06% and less than 1.0% by weight of electrolyte in the reservoir. More preferably, the concentrations of ions is present in a range from about 0.146% (Example 9) to about 0.9% (Examples 6 and 12–14) by weight of electrolyte in the reservoir.

D. The Ionizable Substance (Drug) for Iontophoretic Delivery.

An ionic drug can be delivered from either the anode, the cathode, or both simultaneously. For example, if the ionic substance to be driven into the body is positively charged, then the positive electrode or anode will be the active electrode and the negative electrode or cathode will serve to complete the electrochemical circuit. Alternatively, if the ionic substance to be delivered is negatively charged, then the negative electrode will be the active electrode and the positive electrode will be the indifferent electrode. Alternatively, the drug formulation may contain an amount of an ion which will compete with the ionized or ionizable drug, the amount of the ion should be sufficient for controlling the flux profile of the ionized or ionizable drug been delivery. Preferably, the concentration of ions is an amount greater than about 0.06% and less than 1.0% by weight of electrolyte in the reservoir. More preferably, the concentrations of ions is present in a range from about 0.146% (Example 9) to about 0.9% (Examples 6 and 12–14) by weight of electrolyte in the reservoir.

E. Protective Backing

The iontophoretic apparatus of the invention may also include a suitable backing film positioned on top of the electrolyte reservoir. The backing film provides protection against contamination and damage to the current distributing member, if present, and the electrolyte reservoir of the apparatus.

F. Release Liner

The iontophoretic apparatus of the invention optionally includes a release liner which may be fixed to the underside of the ionized substance reservoir by an adhesive. The release liner protects the surface of the ionized substance reservoir which contact the epithelial surface from contamination and damage when the device is not in use. When the device is ready for use, the release liner may be peeled off to expose the epithelial contacting surface of the ionized reservoir for application of the device to a patient.

G. Indifferent Electrode

Iontophoretic devices require at least two electrodes to provide a potential to drive drug ions into the skin of a patient. Both electrodes are disposed to be in intimate electrical contact with the skin thereby completing the electrochemical circuit formed by the anode pad and cathode pad of the iontophoretic device. The electrode pads may be further defined as an active electrode from which an ionic drug is delivered into the body. An indifferent or ground electrode serves to complete the electrochemical circuit. Various types of electrodes may be employed such as is described in United States application entitled Low-Cost Electrodes for Iontophoretic Device, by Reddy et al., Serial No. 08/536,029 filed Sept. 29, 1995.

As depicted in FIG. 1 an embodiment of the iontophoretic device of this invention 50 is configured as follows:

an anode patch 10, having an anode electrode compartment 11 in ionic communication with a skin contacting compartment 13. The skin contacting compartment 13 and the anode electrode compartment 11 maybe separated by a compartment separation means (membrane) 17. The anode electrode compartment 11 also contains an anode 14 and an electrolyte (anolyte) 15. The skin contacting compartment is attached to the patient's skin 36. A cathode patch 20, having a cathode electrode compartment 21 in ionic communication with a skin contacting compartment 23. The skin contacting compartment 23 and the cathode electrode compartment 21 may be separated by a compartment separation means (membrane) 27. The cathode electrode compartment 21 also contains a cathode 24 and an electrolyte (catholyte) 25. The skin contacting compartment is attached to the patient's skin 36.

While the present invention has been described in connection with iontophoresis, it should be appreciated that it may be used in connection with other principles of active introduction, i.e., motive forces. Accordingly, the invention is understood to be operative in connection with electrophoresis, which includes the movement of particles in an electric field toward one or the other electric pole (anode or cathode), and electroosmosis, which includes the transport of uncharged compounds due to the bulk migration of water induced by an electric field. Also it should be appreciated that the patient or subject may include humans as well as animals.

EXAMPLES

Example 1

In vitro Excised Skin Delivery Experiments

Patch Designs:

The two compartment patch design includes an absorbent drug reservoir with 2 $cm^2$ skin-contacting area and volume of 0.30 mL. The drug reservoir is separated from the electrode compartment with a 100 MWCO ultrafiltration membrane. The electrode compartment included a silver anode and cation exchange media in a hydrogel. A monolithic patch design was also used, consisting of a sandwich composed of a silver anode in the middle of 2 layers of absorbent material. The patches are assembled and loaded with the dosing solution just before applying to the skin.

Experimental Protocol:

The iontophoretic delivery of a receptor agonist was carried out in a flow-through in vitro system. A silver chloride mesh return cathode was located upstream of the polycarbonate flow-through cells. Freshly dermatomed (1 mm) porcine skin was mounted in the cells on a porous support. The patches were dosed with aqueous solutions of the drug and then placed on top of the excised skin. The patches were secured by a spring loaded mechanism which maintained even pressure over the patch. The cells were "perfused" by means of a peristaltic pump which pulls receiver solution through them. Effluents from the cells were collected with a fraction collector. Flow rates were typically 0.25 min. The receiver solution was an isotonic pH 7.4 buffered saline solution containing 10 mM HEPES, 100 mM NaCl, PEG400, and a surfactant, Pluronic P-103. Iontophoresis current was provided by WIP power cells, and the applied currents and cell voltages were recorded with a Fluke databucket.

Figure 2:
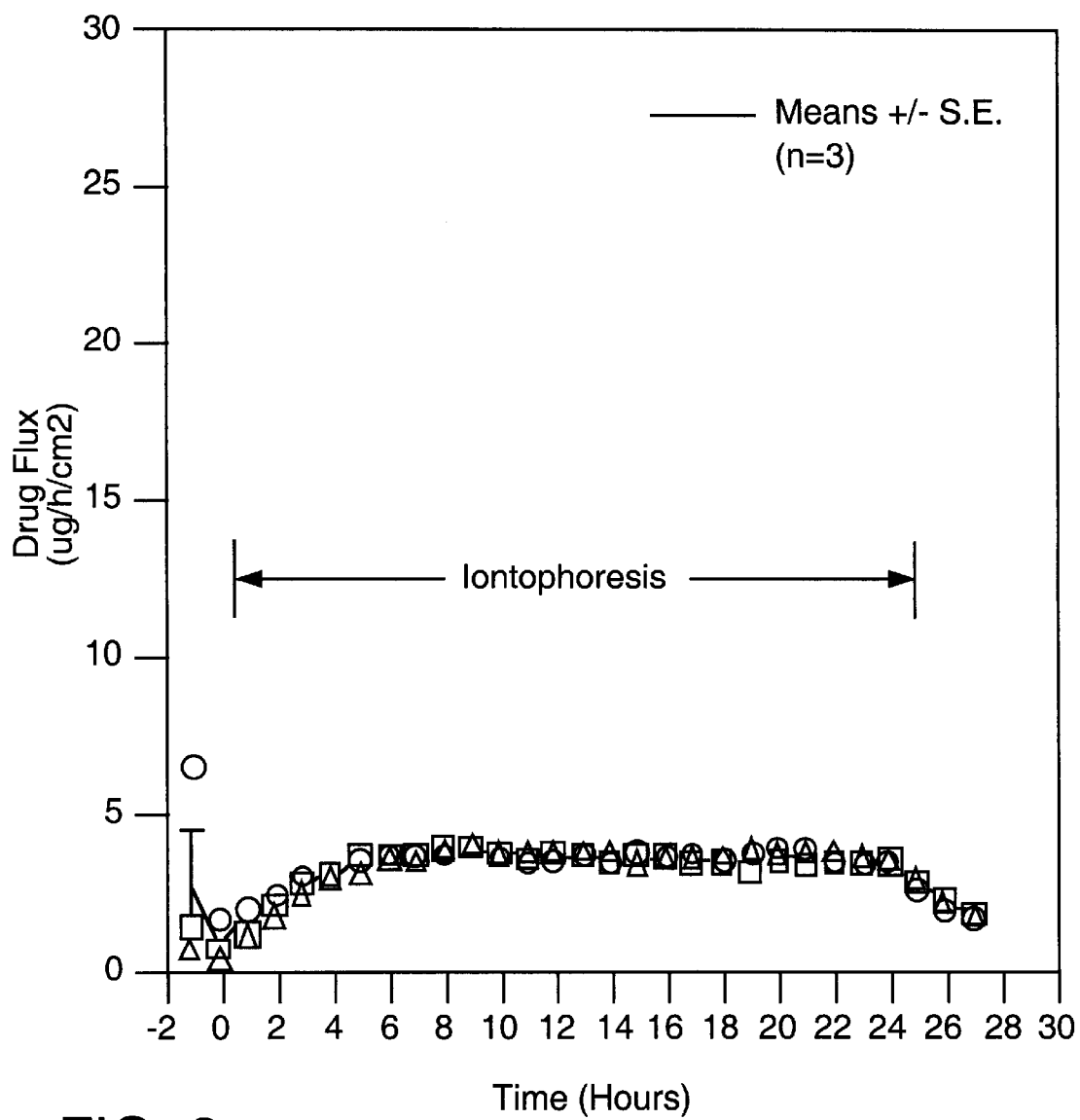
FIG. 2 depicts in vitro delivery with 10 mg/mL of a GPIIb/IIIa receptor antagonist and 154 mM NaCl at 50 μA with 2 cm².
Figure 3:
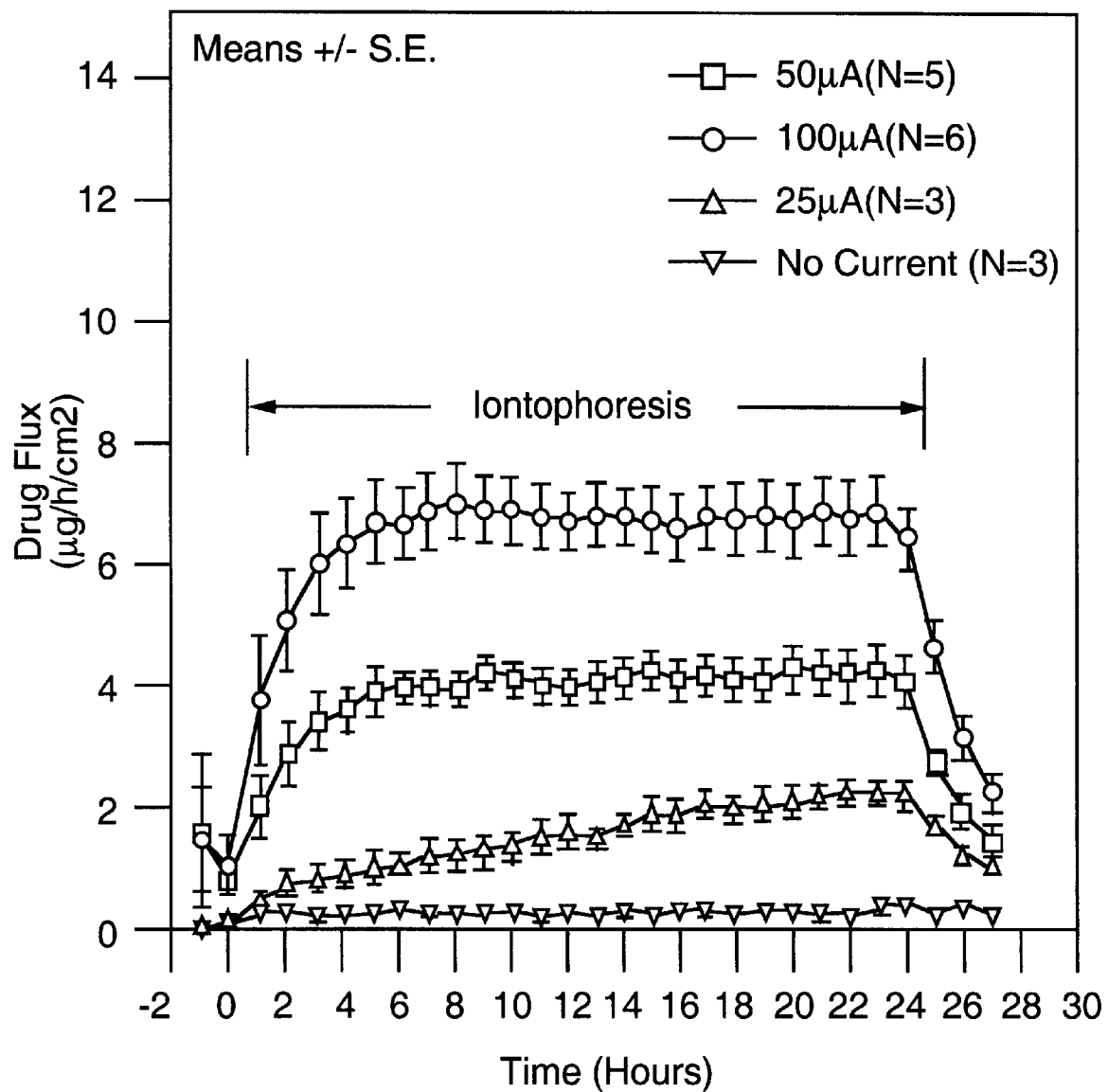
FIG. 3 depicts Iontophoretic delivery across excised pig skin of a 10 mg/mL positively charged ester drug (GPIIb/IIIa receptor antagonist) and 9 mg/mL NaCl to therapeutic flux levels (1–10 μg/h).
Figure 4:
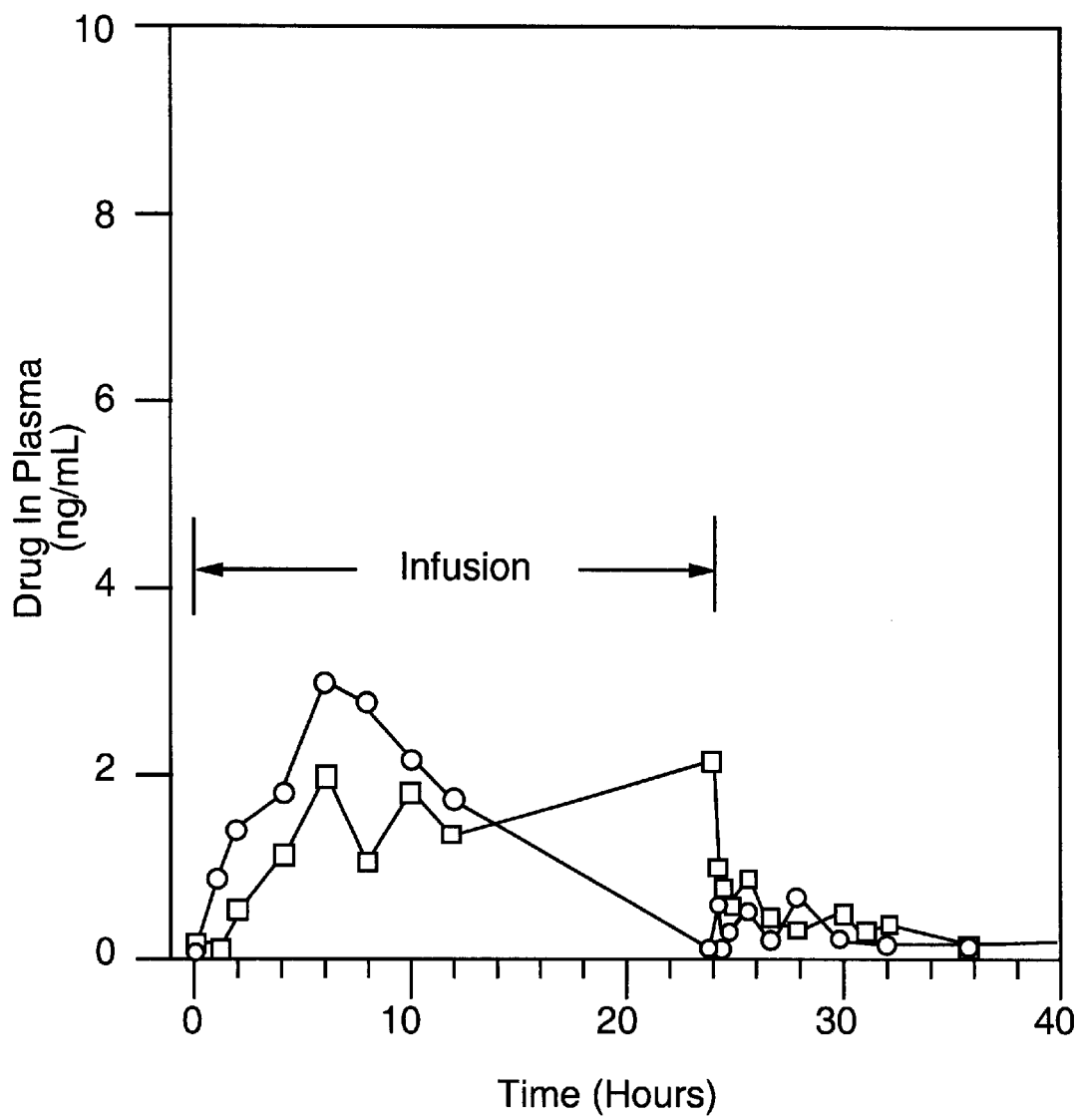
FIG. 4 depicts plasma concentrations of the acid drug form during IV infusion of the acid drug form at a rate equivalent to 10 μg/h active component of the GPIIb/IIIa receptor antagonist in unanesthetized swine.
Figure 5:
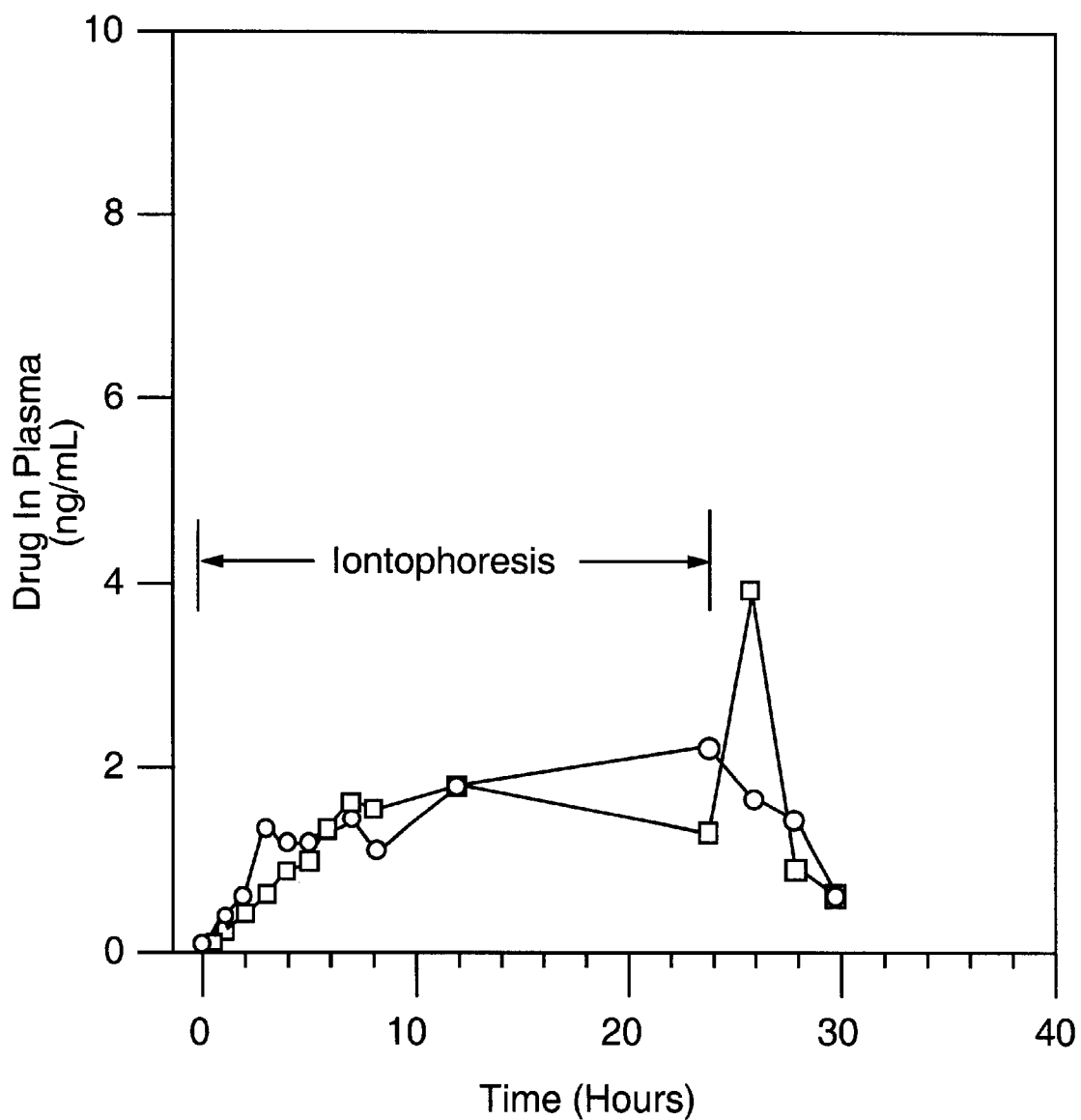
FIG. 5 depicts plasma concentration of the GPIIb/IIIa receptor antagonist acid drug form following iontophoretic delivery in an unanesthetized swine using a 2 cm² patch with 20 mg/mL of GPIIb/IIIa receptor antagonist and 154 mM NaCl at 200 μA.

Results:

FIG. (2) demonstrates that iontophoresis is a capable means for delivering GPIIb/IIIa receptor antagonists to constant flux levels over a period of 24 hours. In particular, FIG. 2 shows a steady drug flux of about 3.5 $\mu g/h/cm^2$ during the 4 to 24 hour period after the beginning of iontophoretic delivery. The variability in delivery from skin to skin is also low. Figure (3) shows that the in-vitro delivery is proportional to current and that the flux is very constant over the 24 hours period. In these experiments the flux reaches steady state rapidly and it is also evident that flux levels drop rapidly on termination of the current. In particular, FIG. 3 shows a steady drug flux during the 4 to 24 hour period after the beginning of iontophoretic delivery.

Example 2

In vivo Swine Experiments

Patch Design:

Same as above.

Experimental Protocol:

In each experiment, the patches were loaded with drug solution immediately before application to the skin of the animals. Unanesthetized Yorkshire swine with weights from 20–35 kg were used. The skin sites receiving the patches were wiped clean with moist gauze pads. Patches were over wrapped with an adhesive, elastic wrap to hold the patches in place. Separate constant current power supplies were provided for each iontophoresis patch system. Current and voltage readings were made and recorded by a Fluke data bucket. Blood samples were withdrawn from the vena cava through an IV catheter into VACUTAINER™ blood collection tubes containing EDTA. After gently mixing, the tubes were centrifuged to separate the plasma, which was transferred to clean polypropylene tubes and frozen on dry ice. Frozen samples were stored at–80 C until assayed.

Results:

FIGS. (4) and (5) show the comparison of the in-vivo delivery of the GPIIb/IIIa to pigs using constant iontophoresis and constant IV infusion. The results show that blood levels obtained from both delivery techniques is similar and the variability in plasma levels seen with the iontophoreses is low.

Example 3

Figure 6:
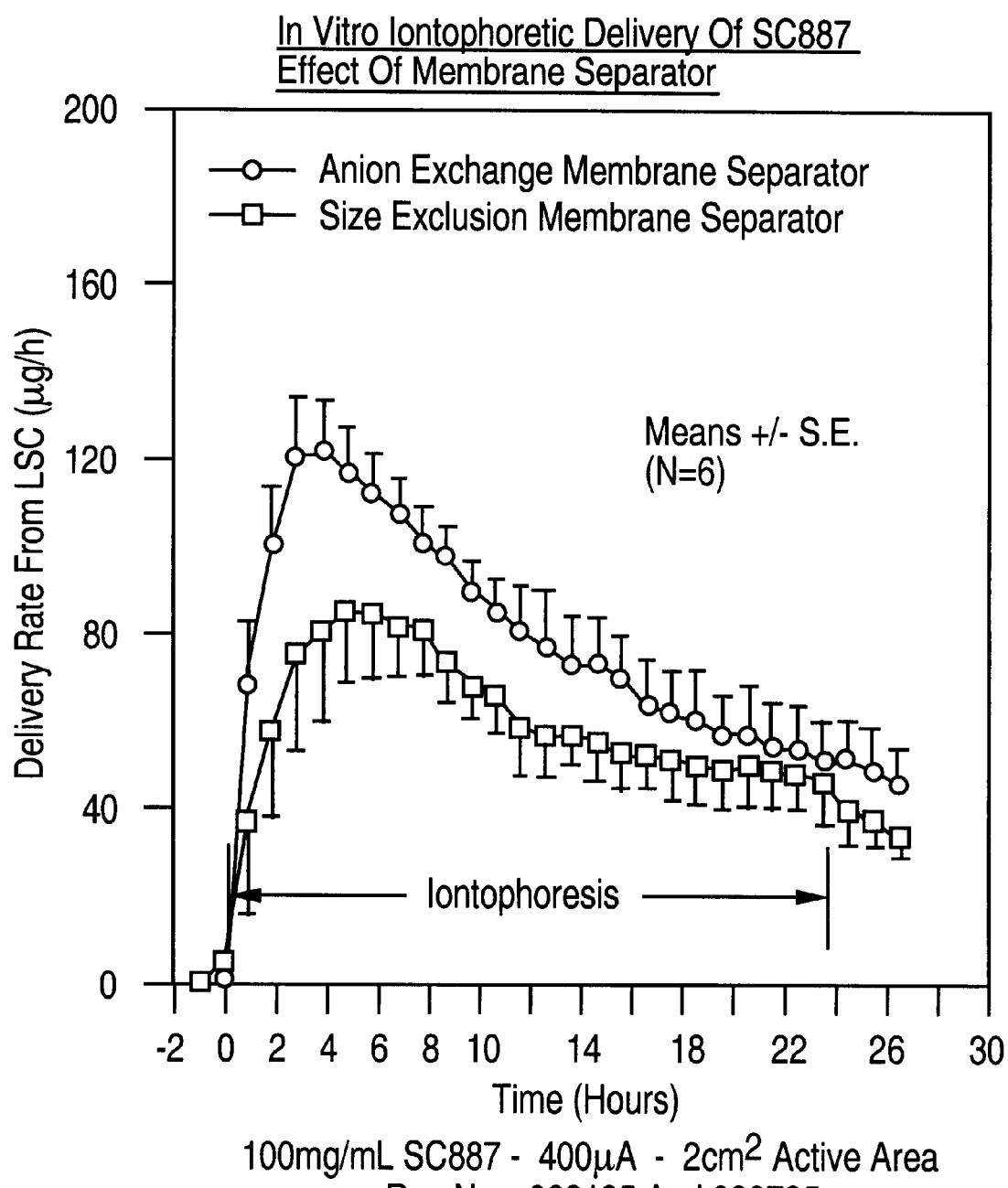
FIG. 6 compares the delivery rate profiles for the dual compartment patches at a current of 400 μA.
Figure 7:
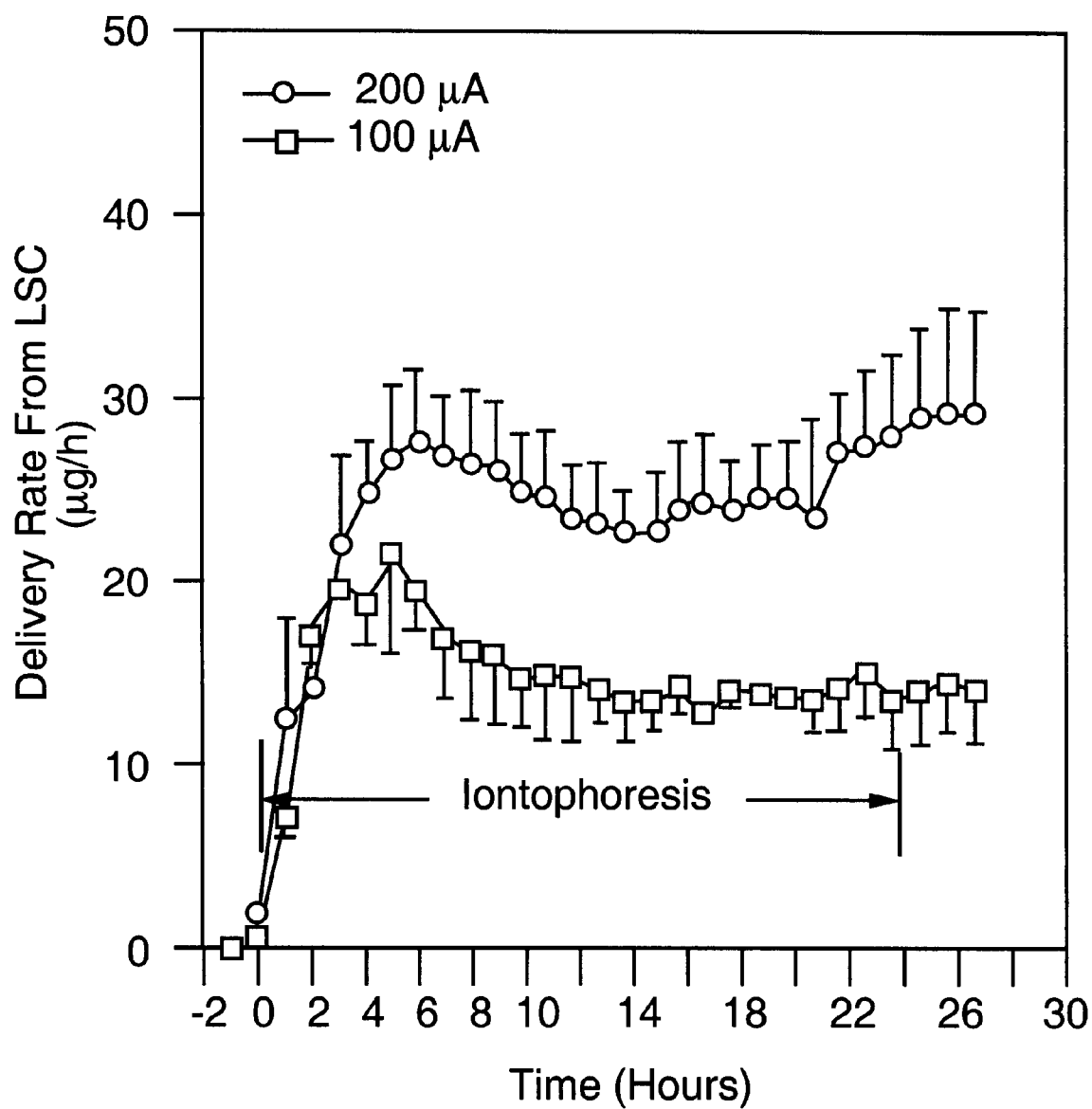
FIG. 7 depicts the delivery profile of dual compartment patches loaded with 50 mg/mL chloride salt and run at a current of 100 μA. and 200 μA.
Figure 8:
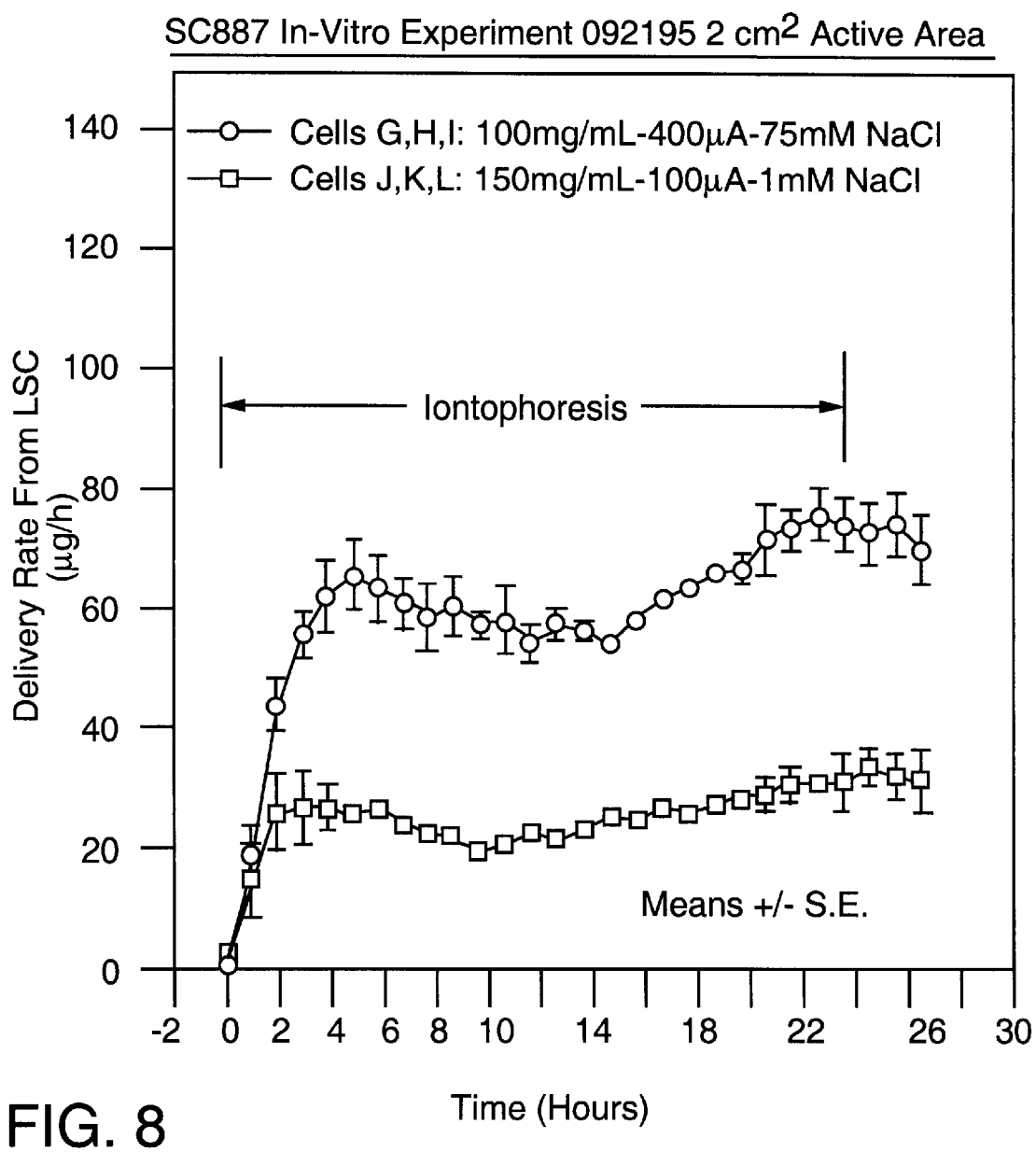
FIG. 8 depicts the delivery rate profile of dual compartment patches loaded with 1 mM NaCl, 150 mg/mL formulation and run at a current of 100 μA. and loaded with 75 mM NaCl, 100 mg/mL formulation and run at a current of 400 μA.

In vitro Iontophoretic delivery of GPIIb/IIIa antagonist, effect of Membrane Separator Rationale:

Because of the choices of saline concentration, and the fact that any electrolyte ion in the drug reservoir which is a cation will compete for current with the drug, the patch design can fall into one of three profiles:

a) bolus or peaked profile: this is obtained by using a low or near zero saline concentration. With few or no other cations to compete with drug cations in the reservoir, the flux will start high and then fall as electrolyte cations accumulate with time in the drug reservoir and then, as shown in FIG. 6 (10 mM saline), a steady drug delivery profile is obtained from 12 to 24 hours after the beginning of iontophoretic delivery;

b) a nearly a flat profile: if the reservoirs contain about 75 mM saline at the start, then the saline concentration will neither increase nor decrease, and a steady flux will be obtained, or c) a profile which increases with time: similarly, if a high saline concentration is started with, then the saline concentration will fall with time, and due to competition for the current, the drug flux will increase with time.

Patches:

A dual compartment 2 $cm^2$ patch design, loaded with 100 mg/mL GPIIb/IIIa antagonist, with a size exclusion or anion exchange membrane separator.

Experimental Protocol:

See example 1, with current applied at 400 $\mu A$.

Results:

FIG. (6) compares the delivery rate profiles for the dual compartment patches at 400 $\mu A$. While the anion exchange membrane patch provided somewhat greater delivery, the two profiles are similar. These results fit the bolus or peaked profile, the flux starts high, and falls as electrolyte cations accumulate with time. In particular, as can be seen in FIG. 6, the flux increases from 0 to 120 μg/h during the first four hours of iontophoretic delivery and steadily falls to 40 μg/h by the twenty-sixth hour of iontophoretic delivery.

Example 4

In vitro Iontophoretic delivery of GPIIb/IIIa antagonist, effect of chloride salt Patches:
A dual compartment 2 cm² patch design, loaded with 50 mg/mL chloride salt.
Experimental Protocol:
See example 1, current applied at 100 μA and 200 μA.
Results:
The delivery rate profiles for these runs are shown in FIG. (7). The results at 100 μA show nearly flat delivery at 10–20 μg/h. The run at higher current (200 μA) also gave nearly constant delivery in the 20–35 μg/h range. These results fit the nearly flat profile and a steady flux is obtained during the 6 to 27 hour period after the beginning of iontophoretic delivery.

Example 5

In vitro Iontophoretic delivery of GPIIb/IIIa antagonist, effect of current, drug concentration, and salinity Patches:
A dual compartment 2 cm² patch design, loaded with either a 1 mM NaCl, 150 mg/mL formulation, or a 75 mM NaCl, 100 mg/mL formulation.
Experimental Protocol:
See example 1, current applied at either 100 μA or 400 μA.
Results:
The delivery rate profiles for these conditions are compared in FIG. (8). The profiles at 100 μA and 400 μA both show an improvement over the earlier profiles, providing much more uniform delivery rates for the 24 hour duration of iontophoresis during the 4 to 26 hour period after the beginning of iontophoretic delivery.

Example 6

Figure 9B:
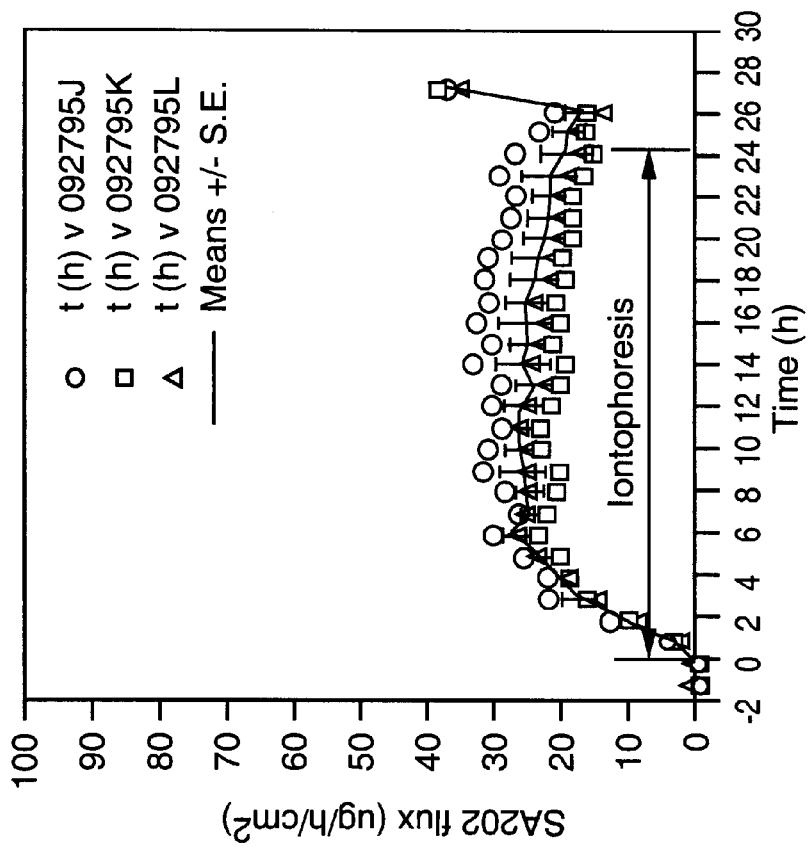
FIG. 9B depicts the delivery rate profile of a dual compartment patch loaded with a 154 mM NaCl, 150 mg/mL formulation and run at a current of 250 µA.
Figure 9A:
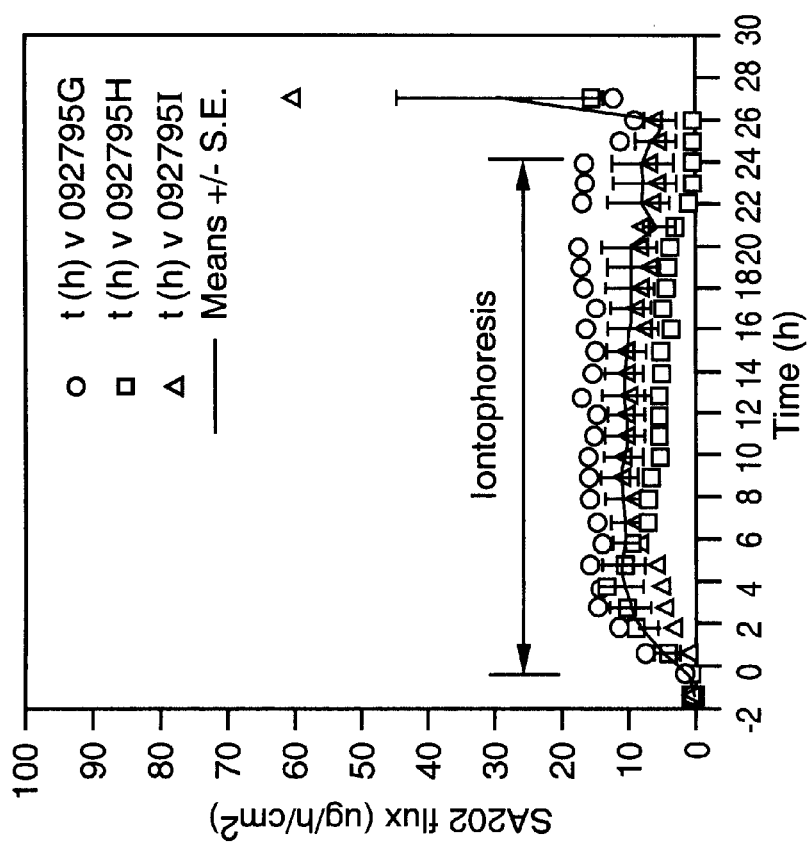
FIG. 9A depicts the delivery rate profile of a dual compartment patch loaded with a 154 mM NaCl, 50 mg/mL formulation and run at a current of 250 μA.

In vitro Iontophoretic Delivery of GPIIb/IIIa Antagonist, Effect of Chloride salt Patches:
A dual compartment 2 cm² patch design, loaded with 154 mM NaCl, 50 mg/mL chloride salt and a dual compartment 2 cm² patch design, loaded with 154 mM NaCl, 150 mg/mL chloride salt.
Experimental Protocol:
See Example 1, current applied at 250 μA.
Results:
The delivery rate profiles for the dual compartment patches are shown in FIGS. 9A and 9B. At a NaCl concentration of 154 mM, the results show a greater rate of delivery with the patch having the higher drug concentration of 150 mg/mL chloride salt (FIG. 9B) than with the patch having a drug concentration of 50 mg/mL chloride salt (FIG. 9A). In particular, FIG. 9B shows a nearly flat delivery profile of 20–25 ug/h during the 4 to 24 hour period after the beginning of iontophoretic delivery whereas FIG. 9A shows a nearly flat delivery profile of 10 ug/h during the 4 to 24 hour period after the beginning of iontophoretic delivery.

Example 7

In vitro Iontophoretic Delivery of GPIIb/IIIa Antagonist, Effect of Chloride Salt at a High NaCl Concentration Patches:
A dual compartment 2 cm² patch design, loaded with 250 mM NaCl, 50 mg/mL chloride salt and a dual compartment 2 cm² patch design, loaded with 250 mM NaCl, 150 mg/mL chloride salt.
Experimental Protocol:
See Example 1, current applied at 250 μA.
Results:
The delivery rate profiles for the dual compartment patches are shown in FIGS. 10A and 10B. At a high NaCl concentration, the results show a greater rate of delivery with the patch having a drug concentration of 150 mg/mL chloride salt (FIG. 10B) than with the patch having a drug concentration of 50 mg/mL chloride salt (FIG. 10A). In particular, FIG. 10B shows a nearly flat delivery profile of about 27 ug/h during the 4 to 24 hour period after the beginning of iontophoretic delivery whereas FIG. 10A shows a nearly flat delivery profile of 15 ug/h during the 4 to 24 hour period after the beginning of iontophoretic delivery. Accordingly, a patch having a high drug concentration and high NaCl concentration provides desirable results.

Further, comparing FIGS. 9B and 10B which show the profiles of patches having a 150 mg/mL drug concentration at a current of 250 μA, it is apparent that desirable results are obtained at a higher NaCl concentration. In particular, FIG. 10B (250 mM NaCl concentration) shows a much smoother profile than FIG. 9B (154 mM NaCl concentration).

Example 8

In vitro Iontophoretic Delivery of GPIIb/IIIa Antagonist, Effect of Current

Figures 11A, 11B:
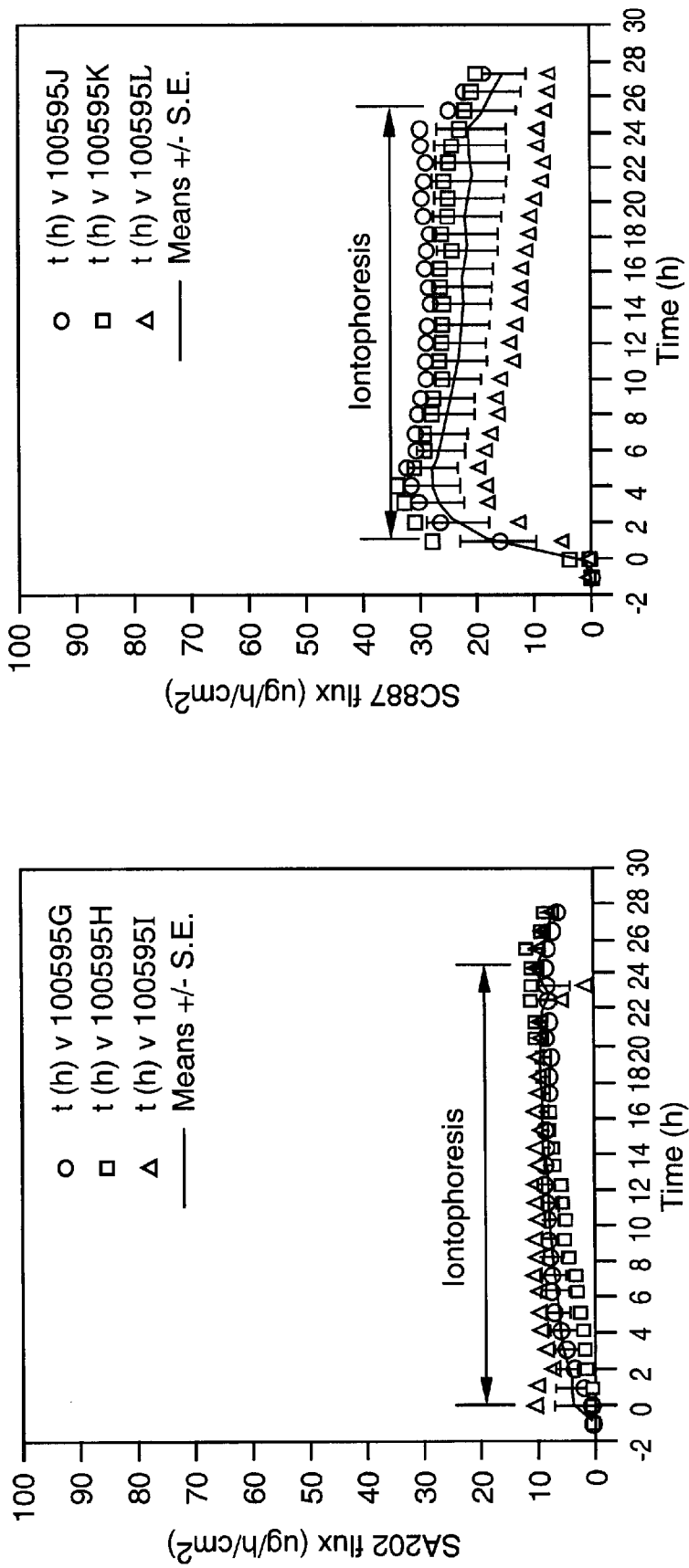
FIG. 11A depicts the delivery rate profile of a dual compartment patch loaded with a 87.5 mM NaCl, 50 mg/mL formulation and run at a current of 100 µA.
FIG. 11B depicts the delivery rate profile of a dual compartment patch loaded with a 87.5 mM NaCl, 50 mg/mL formulation and run at a current of 400 µA.

Patches:
Dual compartment 2 cm² patch designs, loaded with 87.5 mM NaCl, 50 mg/mL chloride salt.
Experimental Protocol:
See Example 1, current applied at 100 μA and 200 μA.
Results:
The delivery rate profiles for the dual compartment patches are shown in FIGS. 11A and 11B. The results show a greater rate of delivery at a current of 200 μA (FIG. 9B) than at a current of 100 μA (FIG. 11A). In particular, FIG. 11B shows a nearly flat delivery profile of 22 to 28 ug/h during the 4 to 24 hour period after the beginning of iontophoretic delivery whereas FIG. 11A shows a nearly flat delivery profile of 5–10 ug/h during the 4 to 24 hour period after the beginning of iontophoretic delivery.

Example 9

Figure 12B:
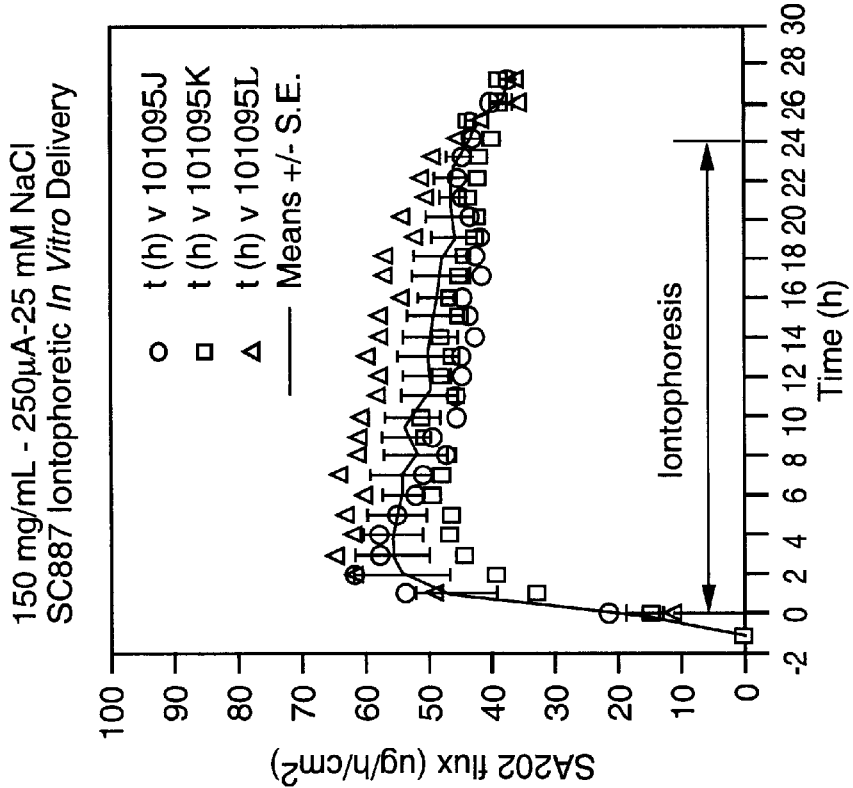
FIG. 12B depicts the delivery rate profile of a dual compartment patch loaded with a 25 mM NaCl, 150 mg/mL formulation and run at a current of 250 µA.
Figure 12A:
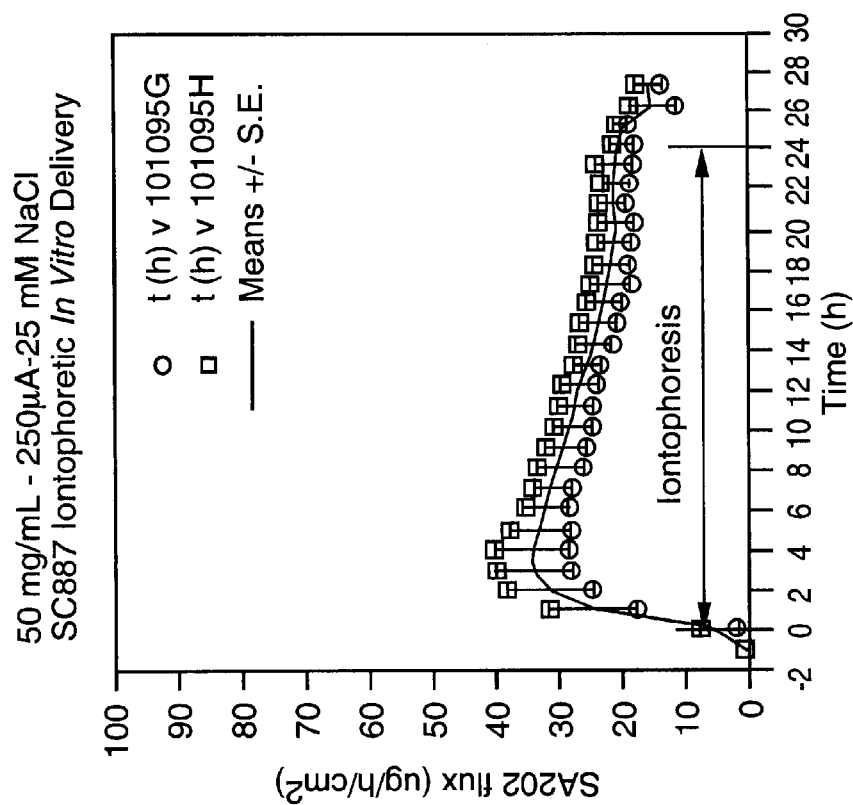
FIG. 12A depicts the delivery rate profile of a dual compartment patch loaded with a 25 mM NaCl, 50 mg/mL formulation and run at a current of 250 µA.

In vitro Iontophoretic Delivery of GPIIb/IIIa Antagonist, Effect of Chloride Salt at a Low NaCl Concentration Patches:
A dual compartment 2 cm² patch design, loaded with 25 mM NaCl, 50 mg/mL chloride salt and a dual compartment 2 cm² patch design, loaded with 25 mM NaCl, 150 mg/mL chloride salt.
Experimental Protocol:
See Example 1, current applied at 250 μA.
Results:
The delivery rate profiles for the dual compartment patches are shown in FIGS. 12A and 12B. At a low NaCl concentration, the results show a greater rate of delivery at a drug concentration of 150 mg/mL chloride salt (FIG. 12B) than at a drug concentration of 50 mg/mL chloride salt (FIG. 12A). In particular, the rate of delivery shown in FIG. 12B falls slowly from about 55 ug/h to about 45 ug/h during the 4 to 24 hour period after the beginning of iontophoretic delivery. The rate of delivery in FIG. 12A falls slowly from about 32–33 ug/h to about 20 ug/h during the 4 to 24 hour period after the beginning of iontophoretic delivery. Further, the drug delivery profiles shown in FIGS. 12A and 12B (25 mM NaCl concentration) are not as smooth as the profiles shown in FIGS. 9A and 9B (154 mM NaCl concentration).

Example 10

In vitro Iontophoretic Delivery of GPIIb/IIIa Antagonist, Effect of Current at a High Drug Concentration Patches:

Dual compartment 2 $cm^2$ patch designs, loaded with 87.5 mM NaCl, 150 mg/mL chloride salt.

Experimental Protocol:

See Example 1, current applied at 100 $\mu$A and 400 $\mu$A.

Figure 13B:
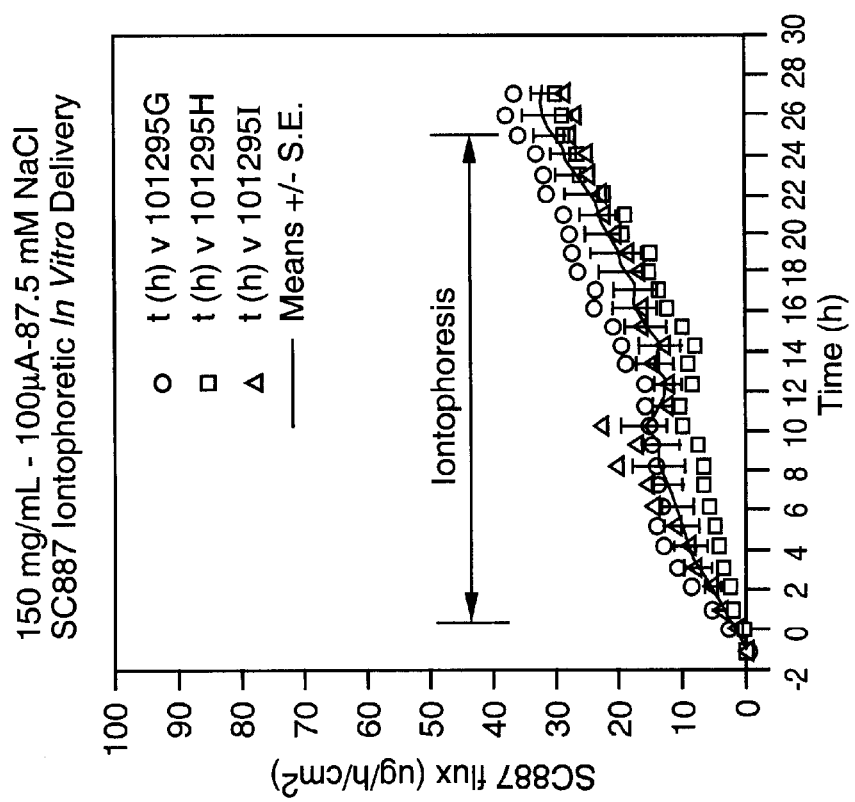
FIG. 13B depicts the delivery rate profile of a dual compartment patch loaded with a 87.5 mM NaCl, 150 mg/mL formulation and run at a current of 400 µA.
Figure 13A:
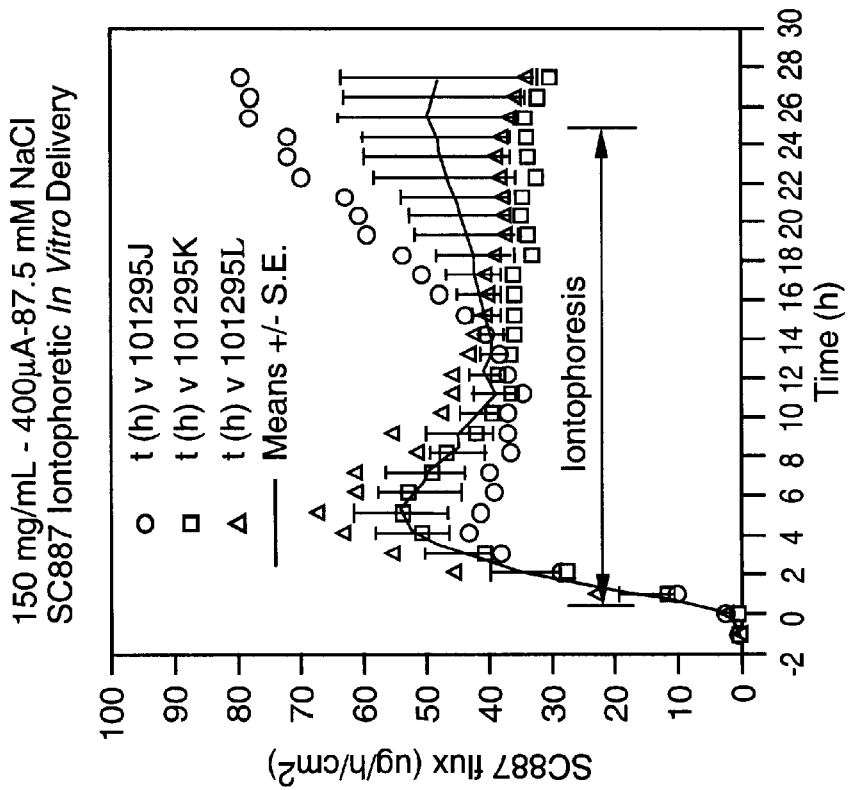
FIG. 13A depicts the delivery rate profile of a dual compartment patch loaded with a 87.5 mM NaCl, 150 mg/mL formulation and run at a current of 100 µA.

Results:

The delivery rate profiles for the dual compartment patches are shown in FIGS. 13A and 13B. The results show a greater rate of drug delivery at a current of 400 $\mu$A (FIG. 13B) than at a current of 100 $\mu$A (FIG. 13A). In particular, the rate of delivery shown in FIG. 13B falls from about 54 ug/h to 40 ug/h, then is smooth and then rises to about 48 ug/h during the 4 to 24 hour period after the beginning of iontophoretic delivery. The rate of drug delivery shown in FIG. 13A rises slowly from about 10 ug/h to about 25 ug/h during the 4 to 24 hour period after the beginning of iontophoretic delivery. Further, the profiles of the patches shown in FIGS. 13A and 13B are not as smooth as the profiles of similar patches with a lower drug concentration, as shown in FIGS. 11A and 11B.

Example 11

In vitro Iontophoretic Delivery of GPIIb/IIIa Antagonist, Effect of NaCl and NaMesylate at a Low Drug Concentration Patches:

A dual compartment 2 $cm^2$ patch design, loaded with 154 mM NaCl, 30 mg/mL chloride salt and a dual compartment 2 $cm^2$ patch design, loaded with 150 mM NaMesylate, 30 mg/mL chloride salt.

Experimental Protocol:

See Example 1, current applied at 150 $\mu$A.

Figure 14B:
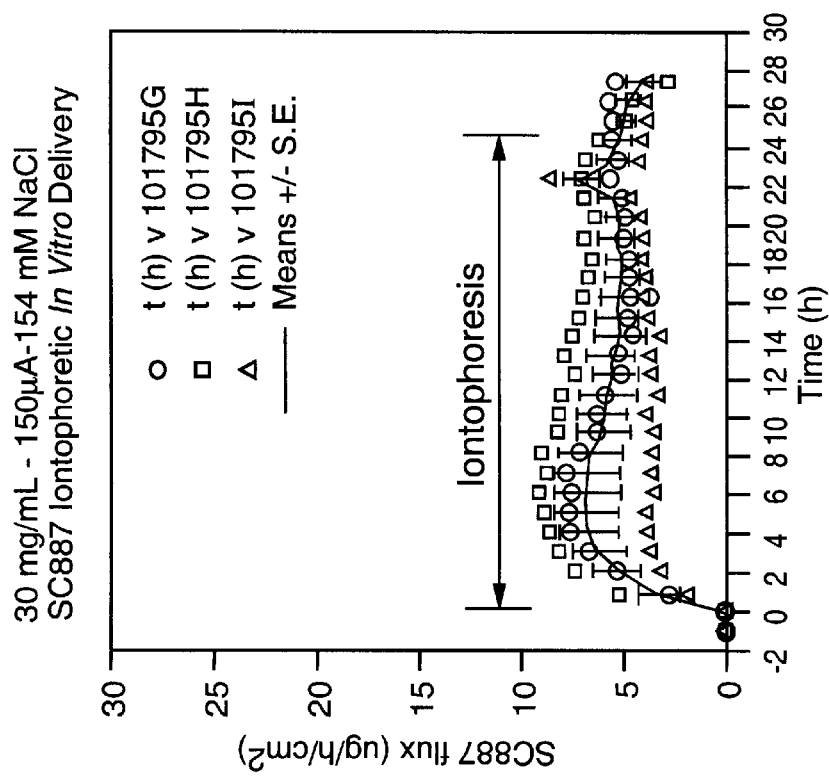
FIG. 14B depicts the delivery rate profile of a dual compartment patch loaded with a 150 mM NaMeasylate, 30 mg/mL formulation and run at a current of 150 µA.
Figure 14A:
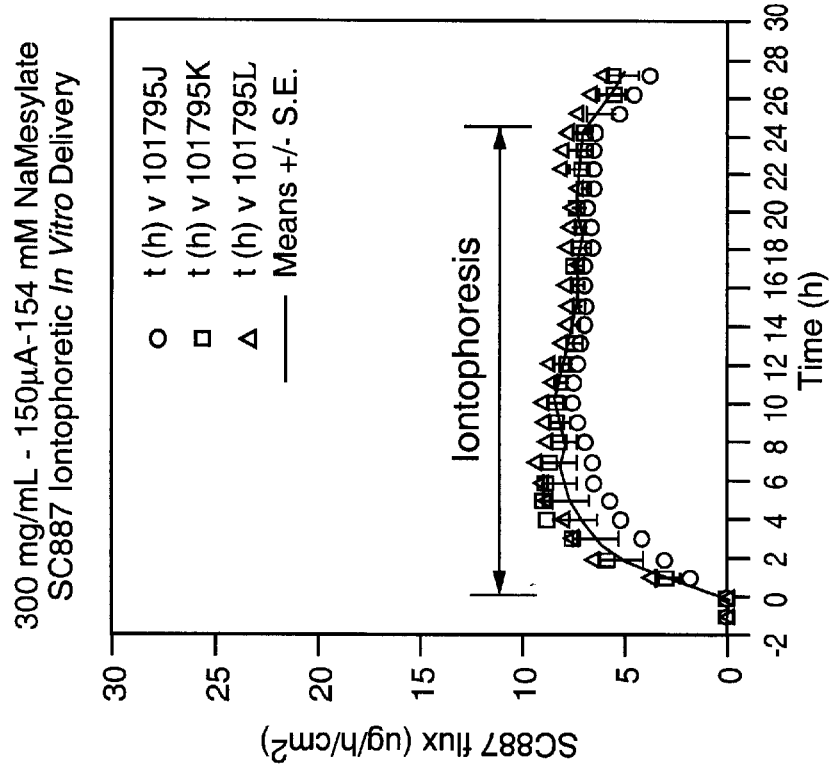
FIG. 14A depicts the delivery rate profile of a dual compartment patch loaded with a 154 mM NaCl, 30 mg/mL formulation and run at a current of 150 µA.

Results:

The delivery rate profiles for the dual compartment patches are shown in FIGS. 14A and 14B. The results show similar drug delivery profiles at a drug concentration of 154 mM NaCl, 30 mg/mL chloride salt (FIG. 14A) and 150 mM NaMesylate, 30 mg/mL chloride salt (FIG. 14B). In particular, FIG. 14A shows a nearly flat delivery profile of 5–7 ug/h during the 4 to 24 hour period after the beginning of iontophoretic delivery and FIG. 14B shows a nearly flat delivery profile of 6–8 ug/h during the 4 to 24 hour period after the beginning of iontophoretic delivery. Accordingly, desirable results can be obtained using different salt solutions.

Example 12

In vitro Iontophoretic Delivery of GPIIb/IIIa Antagonist, Effect of Drug Concentration at a Low Current and a NaCl Concentration of 154 mM Patches:

A dual compartment 2 $cm^2$ patch design, loaded with 154 mM NaCl, 10 mg/mL chloride salt and a dual compartment 2 $cm^2$ patch design, loaded with 154 mM NaCl, 50 mg/mL chloride salt.

Experimental Protocol:

See Example 1, current applied at 50 $\mu$A.

Figure 15B:
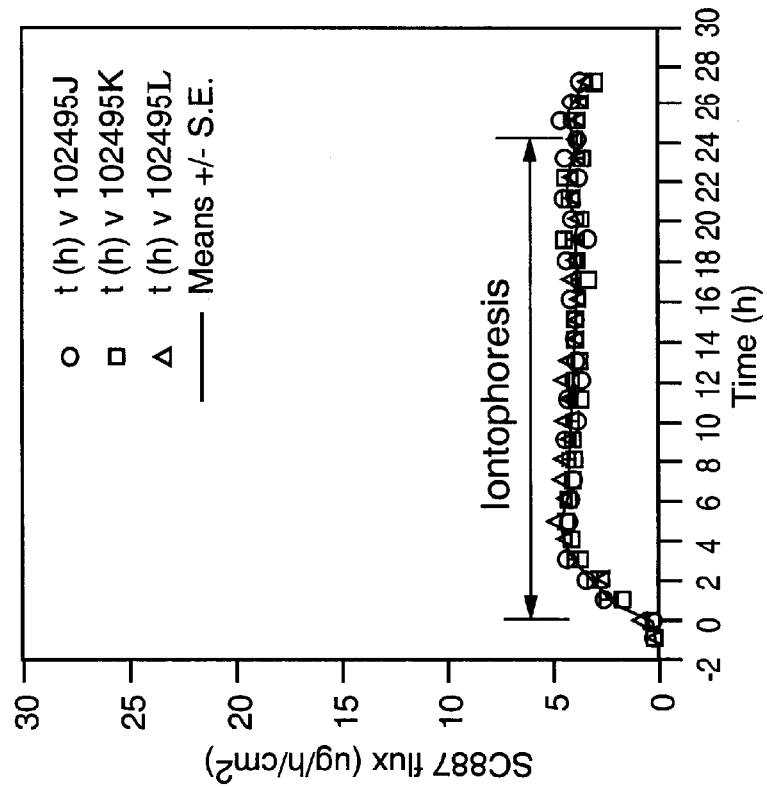
FIG. 15B depicts the delivery rate profile of a dual compartment patch loaded with a 154 mM NaCl, 50 mg/mL formulation and run at a current of 50 µA.
Figure 15A:
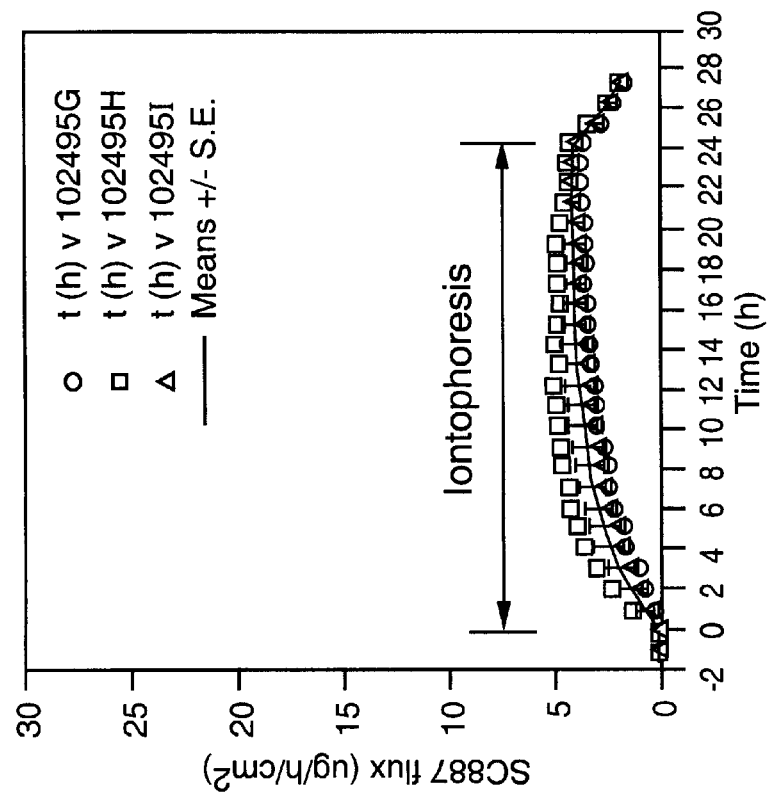
FIG. 15A depicts the delivery rate profile of a dual compartment patch loaded with a 154 mM NaCl, 10 mg/mL formulation and run at a current of 50 µA.

Results:

The delivery rate profiles for the dual compartment patches are shown in FIGS. 15A and 15B. The results show similar drug delivery profiles at drug concentrations of 10 mg/mL chloride salt (FIG. 15A) and 50 mg/mL chloride salt (FIG. 15B) at a low current of 50 $\mu$A. In particular, FIG. 15A shows a nearly flat delivery profile of 3–5 ug/h during the 4 to 24 hour period after the beginning of iontophoretic delivery and FIG. 15B also shows a nearly flat drug delivery profile of about 4 ug/h during the 4 to 24 hour period after the beginning of iontophoretic delivery. The results shown in both FIGS. 15A and 15B fit the nearly flat drug delivery profile. Accordingly, desirable results can also be obtained at currents as low as 50 $\mu$A.

Further, comparing FIG. 9A to FIG. 15B, it is apparent that a smooth drug delivery profile can be obtained with a drug concentration of 50 mg/mL at a NaCl concentration of 154 mM at either a current of 50 $\mu$A (FIG. 15B) or at a current of 250 $\mu$A (FIG. 9A).

Example 13

In vitro Iontophoretic Delivery of GPIIb/IIIa Antagonist, Effect of Drug Concentration at a Current of 250 $\mu$A and a NaCl concentration of 154 mM Patches:

A dual compartment 2 $cm^2$ patch design, loaded with 154 mM NaCl, 10 mg/mL chloride salt and a dual compartment 2 $cm^2$ patch design, loaded with 154 mM NaCl, 50 mg/mL chloride salt.

Experimental Protocol:

See Example 1, current applied at 250 $\mu$A.

Figure 16B:
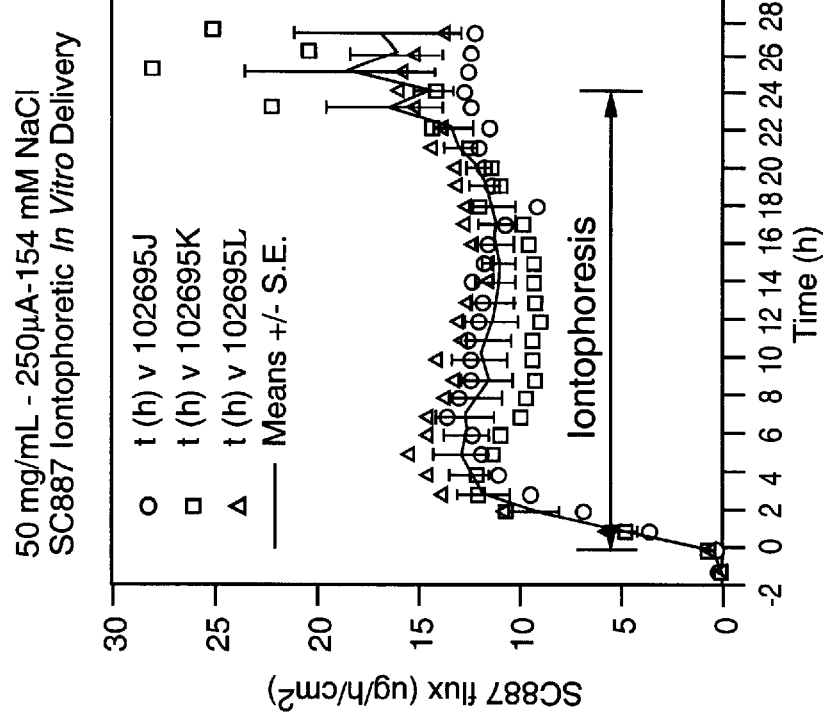
FIG. 16B depicts the delivery rate profile of a dual compartment patch loaded with a 154 mM NaCl, 50 mg/mL formulation and run at a current of 250 µA.
Figure 16A:
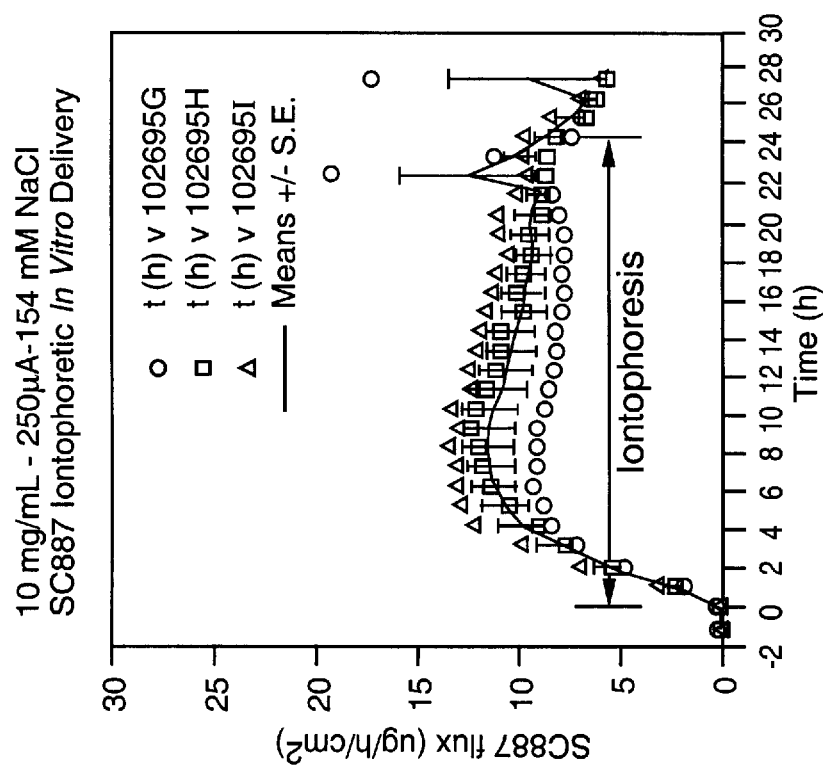
FIG. 16A depicts the delivery rate profile of a dual compartment patch loaded with a 154 mM NaCl, 10 mg/mL formulation and run at a current of 250 µA.

Results:

The delivery rate profiles for the dual compartment patches are shown in FIGS. 16A and 16B. The results show a greater rate of drug delivery at a drug concentration of 50 mg/mL chloride salt (FIG. 16B) than at a drug concentration of 10 mg/mL chloride salt (FIG. 16A). In particular, the rate of drug delivery shown in FIG. 16B falls slightly from about 13 ug/h to 12 ug/h, then is smooth and then rises to about 14 ug/h during the 4 to 24 hour period after the beginning of iontophoretic delivery. The rate of drug delivery shown in FIG. 16A rises slowly from about 10 ug/h and then slowly falls to about 8 ug/h during the 4 to 24 hour period after the beginning of iontophoretic delivery. The results shown in FIGS. 16A and 16B both show a nearly flat drug delivery profile. Accordingly, desirable results can be obtained at low drug concentrations, a 154 mM NaCl concentration and at an intermediate current, such as 250 $\mu$A.

Example 14

In vitro Iontophoretic Delivery of GPIIb/IIIa Antagonist, Effect of a Low Drug Concentration with a NaCl Concentration of 154 mM and at a Current of 100 µA.

Patches:

Dual compartment 2 cm$^2$ patch designs, loaded with 154 mM NaCl, 20 mg/mL chloride salt.

Experimental Protocol:

See Example 1, current applied at 100 µA.

Figure 17B:
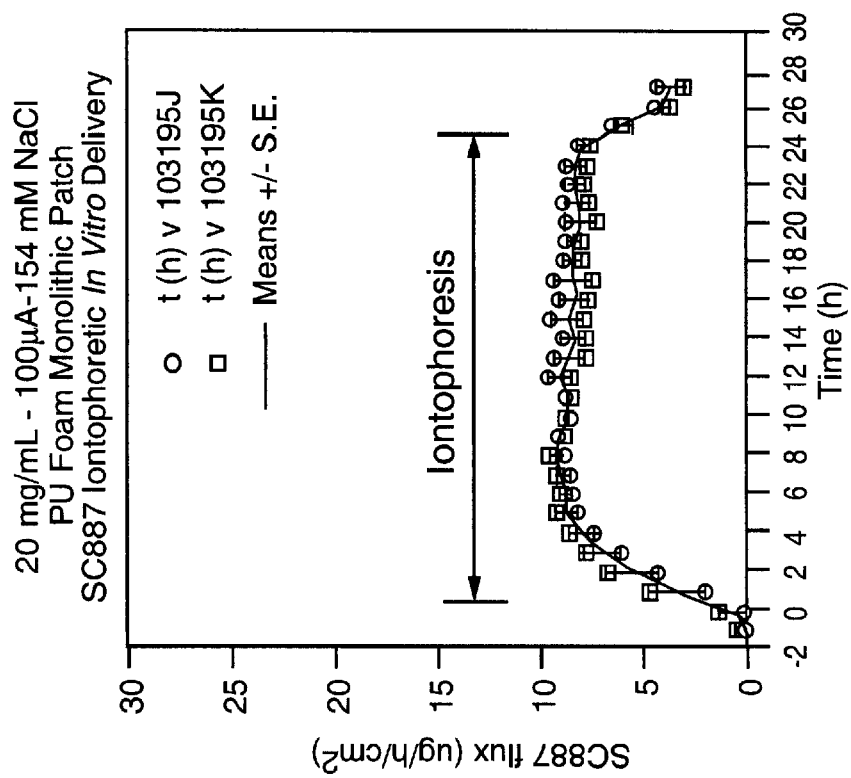
FIG. 17B depicts the delivery rate profile of a dual compartment patch loaded with a 154 mM NaCl, 20 mg/mL formulation and run at a current of 100 µA.
Figure 17A:
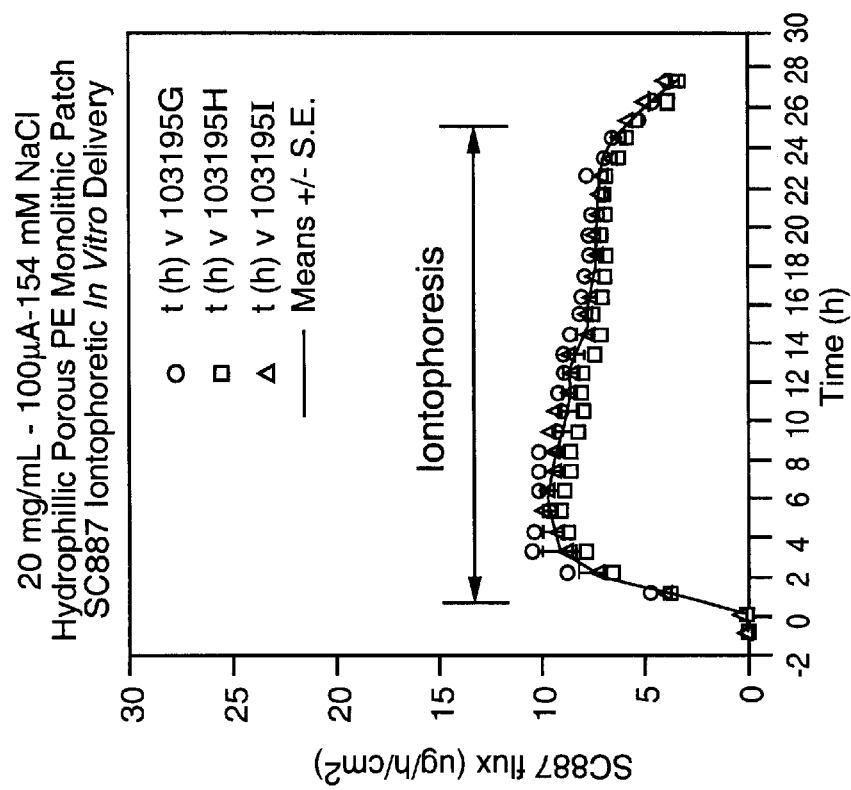
FIG. 17A depicts the delivery rate profile of a dual compartment patch loaded with a 154 mM NaCl, 20 mg/mL formulation and run at a current of 100 µA.

Results:

The delivery rate profiles for the dual compartment patches are shown in FIGS. 17A and 17B. The results show similar drug delivery profiles, as expected, since both patches have identical drug and salt concentrations of 154 mM NaCl, 20 mg/mL chloride salt. In particular, FIG. 17A shows the rate of drug delivery falling from 9 ug/h to 7 ug/h during the 4 to 24 hour period after the beginning of iontophoretic delivery. FIG. 17B shows a flat drug delivery rate of about 8 ug/h during the 4 to 24 hour period after the beginning of iontophoretic delivery. Accordingly, patches having a low drug concentration and a 154 mM NaCl concentration at a moderate to low current of 100 µA provide desirable results.

We claim:

1. A method for controlling the flux profile of an iontophoretically delivered ionized or ionizable drug comprising:

prior to iontophoretic delivery, adding to or having present in a reservoir, which is in ionic communication with said ionized or ionizable drug, ions having a concentration greater than about 0.06% and less than 1.0% by weight of electrolyte in said reservoir which will compete with the ionized or ionizable drug, wherein said reservoir is in electrical communication with an electrode assembly.

2. A method according to claim 1, wherein said ions have a concentration from about 0.146% to about 0.9% by weight of electrolyte in said reservoir.

3. A method according to claim 2, wherein said ions have a concentration of about 0.292% by weight of electrolyte in said reservoir.

4. A method according to claim 2, wherein said ions have a concentration of about 0.438% by weight of electrolyte in said reservoir.

5. A method according to claim 2, wherein said ions have a concentration of about 0.58% by weight of electrolyte in said reservoir.

6. A method according to claim 2, wherein said ions have a concentration of about 0.511% by weight of electrolyte in said reservoir.

7. A method according to claim 2, wherein said ions have a concentration of about 0.877% by weight of electrolyte in said reservoir.

8. A method according to claim 2, wherein said ions have a concentration of about 0.9% by weight of electrolyte in said reservoir.

9. A method according to claim 2, wherein said ions have a concentration of about 0.146% by weight of electrolyte in said reservoir.

10. A method for controlling the flux profile of an iontophoretically delivered positively-charged ionic drug comprising:

forming a reservoir containing said drug with a negatively-charged counter-ion, adding to said reservoir a concentration of cations which compete with said drug for carrying charge from the reservoir to a body surface of a patient, the concentration of cations being greater than about 0.06% and less than 1.0% by weight of electrolyte in said reservoir;

applying to said reservoir an electrically conductive member comprising a sacrificial material readily oxidizable when said conductive member is in contact with said reservoir and a positive voltage is applied to said conductive member, said material when oxidized readily combining with said counter-ion to form a compound which is substantially immobile within said reservoir during the application of said positive voltage; and placing said reservoir containing said drug in drug transmitting relation to the body surface of the patient; and while said reservoir is in drug transmitting relation to the body surface of the patient and the conductive member is applied to said reservoir, applying a positive voltage to said conductive member to oxidize said material and to drive said drug through the body surface of the patient, whereby said drug is driven through the body surface in the presence of said cations which can compete with said drug for carrying charge from the reservoir.

11. A method according to claim 10, wherein said cations have a concentration from about 0.146% to about 0.9% by weight of electrolyte in said reservoir.

12. A method according to claim 11, wherein said ions have a concentration of about 0.292% by weight of electrolyte in said reservoir.

13. A method according to claim 11, wherein said ions have a concentration of about 0.438% by weight of electrolyte in said reservoir.

14. A method according to claim 11, wherein said ions have a concentration of about 0.58% by weight of electrolyte in said reservoir.

15. A method according to claim 11, wherein said ions have a concentration of about 0.511% by weight of electrolyte in said reservoir.

16. A method according to claim 11, wherein said ions have a concentration of about 0.877% by weight of electrolyte in said reservoir.

17. A method according to claim 11, wherein said ions have a concentration of about 0.9% by weight of electrolyte in said reservoir.

18. A method according to claim 11, wherein said ions have a concentration of about 0.146% by weight of electrolyte in said reservoir.

19. A method for controlling the flux profile of an iontophoretically delivered negatively-charged ionic drug comprising:

forming a reservoir containing said drug with a positively-charged counter-ion, adding to said reservoir a concentration of anions which compete with said drug for carrying charge from the reservoir to a body surface of a patient, the concentration of anions being greater than about 0.06% and less than 1.0% by weight of electrolyte in said reservoir;

applying to said reservoir an electrically conductive member comprising a sacrificial material readily reducible when said conductive member is in contact with said reservoir and a negative voltage is applied to the conductive member, said material when reduced readily combining with said counter-ion to form a substance which is substantially immobile within said reservoir during the application of said negative voltage; and placing said reservoir containing said drug in drug transmitting relation to the body surface of the patient; and while said reservoir is in drug transmitting relation to the body surface of the patient and the conductive member is applied to said reservoir, applying said negative voltage to said conductive member to reduce said material and to drive said drug through the body surface of the patient, whereby said drug is driven through the body surface in the presence of said anions which can compete with the drug for carrying charge from the reservoir.

20. A method according to claim 19, wherein said ions have a concentration from about 0.146% to about 0.9% by weight of electrolyte in said reservoir.

21. A method according to claim 20, wherein said ions have a concentration of about 0.292% by weight of electrolyte in said reservoir.

22. A method according to claim 20, wherein said ions have a concentration of about 0.438% by weight of electrolyte in said reservoir.

23. A method according to claim 20, wherein said ions have a concentration of about 0.58% by weight of electrolyte in said reservoir.

24. A method according to claim 20, wherein said ions have a concentration of about 0511% by weight of electrolyte in said reservoir.

25. A method according to claim 20, wherein said ions have a concentration of about 0.877% by weight of electrolyte in said reservoir.

26. A method according to claim 20, wherein said ions have a concentration of about 0.9% by weight of electrolyte in said reservoir.

27. A method according to claim 20, wherein said ions have a concentration of about 0.146% by weight of electrolyte in said reservoir.

28. A method for controlling the flux profile of an iontophoretically delivered ionized or ionizable drug comprising:

prior to iontophoretic delivery, adding to or having present in a reservoir having an ionized or ionizable drug, ions having a concentration greater than about 0.06% and less than 1.0% by weight of electrolyte in said reservoir which will compete with the ionized or ionizable drug, wherein the ionized or ionizable drug and the competing ions are in ionic communication with said reservoir, and wherein said reservoir is in electrical communication with an electrode assembly.

29. A method according to claim 28, wherein said ions have a concentration from about 0.146% to about 0.9% by weight of electrolyte in said reservoir.

30. A method according to claim 29, wherein said ions have a concentration of about 0.292% by weight of electrolyte in said reservoir.

31. A method according to claim 29, wherein said ions have a concentration of about 0.438% by weight of electrolyte in said reservoir.

32. A method according to claim 29, wherein said ions have a concentration of about 0.58% by weight of electrolyte in said reservoir.

33. A method according to claim 29, wherein said ions have a concentration of about 0.511% by weight of electrolyte in said reservoir.

34. A method according to claim 29, wherein said ions have a concentration of about 0.877% by weight of electrolyte in said reservoir.

35. A method according to claim 29, wherein said ions have a concentration of about 0.9% by weight of electrolyte in said reservoir.

36. A method according to claim 29, wherein said ions have a concentration of about 0.146% by weight of electrolyte in said reservoir.

* * * * *